United States Patent [19]

Begley et al.

[11] Patent Number: 5,264,582
[45] Date of Patent: Nov. 23, 1993

[54] METHOD OF FORMING A PHOTOGRAPHIC COUPLER CAPABLE OF FORMING A WASH-OUT DYE

[75] Inventors: William J. Begley, Webster; Robert C. Stewart, Spencerport, both of N.Y.

[73] Assignee: Eastman Kodak Company, Rochester, N.Y.

[21] Appl. No.: 903,782

[22] Filed: Jun. 24, 1992

Related U.S. Application Data

[63] Continuation-in-part of Ser. No. 724,231, Jul. 1, 1991, Pat. No. 5,239,081.

[51] Int. Cl.$^5$ .................... C07D 257/02; G03C 7/26
[52] U.S. Cl. .................... 518/253; 430/382; 430/542; 430/543; 430/544; 518/251; 518/252; 518/267.6
[58] Field of Search ........................ 548/253

[56] References Cited

U.S. PATENT DOCUMENTS

| | | | |
|---|---|---|---|
| 4,248,962 | 2/1981 | Lau | 430/382 |
| 4,409,323 | 10/1983 | Sato et al. | 430/544 |
| 4,482,629 | 11/1984 | Nakagawa et al. | 430/542 |
| 4,861,701 | 8/1989 | Burns et al. | 430/543 |
| 4,959,299 | 9/1990 | Sakanoue et al. | 430/544 |

Primary Examiner—David B. Springer
Attorney, Agent, or Firm—Andrew Alexander

[57] ABSTRACT

A method of preparing a washout photographic coupler comprising a coupler moiety (COUP) containing a substituted or unsubstituted ballasted releasing group (A) selected from aryloxy, thioaryloxy, heterocyclicoxy, and thioheterocyclicoxy releasing groups having attached thereto a phenoxy timing group containing a photographically useful group (PUG), the releasing group capable of elimination electron transfer to release the timing group, the method comprising:

(a) providing a coupler moiety (COUP) having the releasing group (A) in a coupling off position, the releasing group (A) having on at least one of the 2- or 4-position a substituted or unsubstituted halomethyl;

(b) reacting a substituted or unsubstituted hydroxyaryl aldehyde or hydroxyaryl ketone with the halomethyl group of step (a) in the presence of an alkylpyridine and a dipolar aprotic solvent to form a first product; and (c) reducing the first product and halogenating the reduced first product before reacting with a photographically useful group to form the washout photographic coupler.

10 Claims, No Drawings

METHOD OF FORMING A PHOTOGRAPHIC COUPLER CAPABLE OF FORMING A WASH-OUT DYE

This is a continuation-in-art of U.S. Ser. No. 724,231, filed Jul. 1, 1991 now U.S. Pat. No. 5,239,081.

This invention relates to a new photographic coupler that is capable of forming a wash-out dye in a photographic material upon photographic processing to form an image having improved acutance, stability, and interimage effects, and a photographic material and process using such a coupler.

Various ways are recognized in the photographic art for release of a photographically useful group (PUG), such as a color development inhibitor, from a compound, such as a coupler, in a photographic material and process. For example, U.S. Pat. Nos. 4,248,962, and 4,861,701 describes compounds that release photographically useful groups by means of an intramolecular nucleophilic displacement reaction in photographic materials. Other examples of means for release of photographically useful groups are described in, for example, U.S. Pat. Nos. 4,409,323 and 4,861,701. These compounds, particularly couplers, capable of releasing a photographically useful group provide a degree of control over timing and rate of release as well as rate of diffusion and distance of diffusion of the photographically useful group.

The part of the compound that remains in the photographic material after release of the photographically useful group and dye that is formed in the material from reaction with oxidized color developer often provides undesired properties in the photographic material during or after photographic processing. For example the dye formed from a coupler upon release of a photographically useful group often adversely affects the desired image. One answer to this has been to provide a coupler that has a water solubilizing group on the parent coupler to enable the dye formed from the coupler to be washed-out of the photographic element upon photographic processing. Such couplers are described, for example, in U.S. Pat. No. 4,482,629.

A need has existed to provide a coupler, in a photographic material and process that enables formation of an image having improved acutance while enabling removal by wash-out of the dye formed from the coupler during photographic processing. Moreover, such needs have existed with the added parameter that such a compound must not require significantly modifying the development inhibitor group in a way that would adversely effect the ultimate end use of the groups.

Further, such couplers have been difficult to synthesize because the reaction requires specific conditions of base and solvent to enable attachment of the timing group moiety to the releasing group of the coupler.

While the invention has been demonstrated for photographic couplers the synthesis can be used for making other compounds.

The present invention solves these problems by providing a method of preparing a washout photographic coupler comprising a coupler moiety (COUP) containing a substituted or unsubstituted ballasted releasing group (A) selected from aryloxy, thioaryloxy, heterocyclicoxy, and thioheterocyclicoxy releasing groups having attached thereto a phenoxy timing group containing a photographically useful group (PUG), the releasing group capable of elimination electron transfer to release the timing group, the method comprising:

(a) providing a coupler moiety (COUP) having the releasing group (A) in a coupling off position, the releasing group (A) having on at least one of the 2- or 4-position a substituted or unsubstituted halomethyl;

(b) reacting a substituted or unsubstituted hydroxyaryl aldehyde or hydroxyaryl ketone with the halomethyl group of step (a) in the presence of an alkylpyridine and a dipolar aprotic solvent to form a first product; and (c) reducing the first product and halogenating the reduced first product before reacting with a photographically useful group to form the washout photographic coupler.

The halomethyl can be substituted with at least one of hydrogen, substituted or unsubstituted alkyl and substituted or unsubstituted aryl.

The alkylpyridine can be selected from mono-, di-, and trialkylpyridine, such as 2-picoline, 3-picoline, 4-picoline, or 2,4,6-trimethylpyridine and preferably a dialkylpyridine such as 2,4-lutidine.

The dipolar aprotic solvent can be selected from dimethylformamide, dimethylacetamide, and acetonitrile.

In a preferred embodiment potassium iodide can be added to the reaction in step (b) to form an iodomethyl compound thereby increasing the rate of reaction.

The hydroxyaryl aldehyde or hydroxyaryl ketone has the hydroxy group in the 2- or 4-position to the aldehyde or ketone groups.

The halomethyl is bromomethyl or chloromethyl.

A preferred method of the present invention provides a process of forming a compound of the formula:

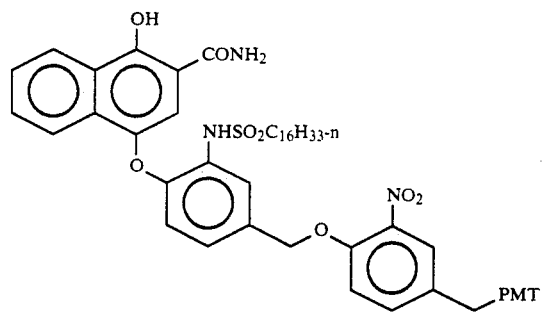

wherein PMT is phenylmercaptotetrazole. The method comprises reacting a compound of formula:

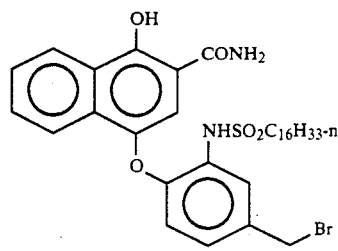

with:

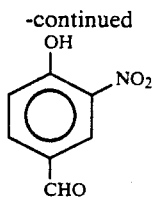

in the presence of 2,6-lutidine indimethylacetamide; then reacting aldehyde product with sodium borohydride to form the corresponding —CH$_2$OH compound; then reacting the resulting —CH$_2$OH compound with PBr$_3$ in ether to form the resulting —Ch$_2$Br compound; and then reacting the resulting —CH$_2$Br compound with sodium phenylmercaptotetrazole.

Typical synthesis steps are illustrated by the reaction steps given for I-13 through I-16.

Further, a photographic element is described comprising a support bearing at least one photographic silver halide emulsion layer and at least one coupler (A) having a water solubilizing group wherein coupler (A) is capable of forming a compound that is washed out of the photographic element during photographic processing and has a coupling-off group represented by the general formula:

wherein;
X is selected from oxygen, nitrogen or sulfur;
X-Rel is a releasing group for releasing T-INH from X-Rel by either intramolecular displacement reaction or electron transfer reaction during photographic processing without substantial delay of releasing;
T is a timing group that releases INH by either elimination electron transfer reaction or intramolecular displacement reaction with timing delay during photographic processing; and
INH is a development inhibitor group.

The X-Rel-T-INH is released from the coupler moiety upon oxidative coupling of the coupler. During photographic processing, the reaction of coupler (A) with oxidized color developing agent cleaves the bond between the coupling-off group and the coupler moiety. Then the bond between X-Rel (RELEASING GROUP) and the T (TIMING GROUP) is cleaved without substantial delay of release. The bond between the T and the INH is then cleaved with timing delay. The cleavage of the bond between the INH and the T can be enabled by for example, an elimination such as the one described in U.S. Pat. Nos. 4,409,323 and 4,959,299, or for example, by an intramolecular displacement reaction, such as one described in, U.S. Pat. No. 4,248,962. Choosing substituent parts of the X-Rel and T to requirements of the given INH allows control over the timing and rate of release of the INH.

The inventions are described in classes in more specific details as follows:

Class 1

In the first invention a photographic element, as noted, is provided comprising a support bearing at least one photographic silver halide emulsion layer and at least one coupler (A) having a water solubilizing group wherein coupler (A) is capable of forming a compound that is washed out of the photographic element during photographic processing. Coupler (A) has a coupling-off group represented by the formula:

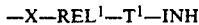

wherein;
X is selected from oxygen, nitrogen or sulfur
X-Rel$^1$ is a releasing group for releasing T$^1$-INH from X-Rel$^1$ by intramolecular displacement reaction during photographic processing without substantial delay of releasing;
T$^1$ is a timing group that releases INH by elimination electron transfer reaction with timing delay during photographic processing; and
INH is a development inhibitor group.

The X-Rel$^1$ as described is any X-Rel$^1$ releasing group which releases T$^1$-INH from X-Rel$^1$ by an intramolecular displacement reaction during photographic processing without substantial delay of releasing. The X-Rel$^1$ as described is not a timing group that substantially delays release of T$^1$-INH. The X-Rel$^1$ can serve as a carrier for a photographic ballast group for the coupler prior to exposure and photographic processing.

A typical X-Rel$^1$ group is represented by the formula:

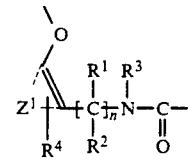

wherein;
R$^1$ and R$^2$ is selected from hydrogen, substituted or unsubstituted alkyl, and substituted or unsubstituted aryl;
R$^3$ is unsubstituted or substituted alkyl or substituted or unsubstituted aryl;
R$^4$ is hydrogen or a substituent which does not substantially delay release of T$^1$-INH;
Z$^1$ represents the atoms necessary to complete a 5 or 6 member aryl or heterocyclic group; and
n is 0, 1 or 2.

A substituent which does not substantially delay release of T$^1$-INH and the substituted or unsubstituted alkyl and substituted or unsubstituted aryl, may be selected from nitro, hydrogen, amino, substituted amino, carboxylic acid, sulfonic acid, methoxy, chloro, bromo, ester groups such as —CO$_2$CH$_3$, keto groups such as —COCH$_3$, or —NHCOCH$_3$, —CONHCH$_3$, —NHSO$_2$CH$_3$, or —SO$_2$NHCH$_3$.

At least one of R$^1$, R$^2$, R$^3$ and R$^4$ can be a photographic ballast group.

The T$^1$ as described is any timing group that releases INH by an elimination electron transfer reaction that enables a time delay between the oxidative coupling of the coupler (A) and the release of INH. The T$^1$ differs from the X-Rel$^1$ in that T$^1$ enables time delay whereas X-Rel$^1$ does not enable substantial time delay.

A typical T$^1$ is represented by the formula

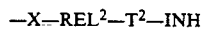 ortho or para to O wherein
$Z^2$ represents the atoms necessary to complete a 5 or 6 member arylene or heterocyclic group;
$R^5$ and $R^6$ is selected from hydrogen, substituted or unsubstituted alkyl or substituted or unsubstituted aryl;
$R^7$ is hydrogen or a substituent which does not substantially delay release of $T^1$-INH from X-Rel$^1$.

A substituent which does not substantially delay release of $T^1$-INH, the substituted or unsubstituted alkyl and substituted or unsubstituted aryl, may be selected from nitro, hydrogen, amino, substituted amino, carboxylic acid, sulfonic acid, methoxy, chloro, bromo, ester groups such as $-CO_2CH_3$, keto groups such as $-COCH_3$, or $-NHCOCH_3$, $-CONHCH_3$, $-NHSO_2CH_3$, or $-SO_2NHCH_3$.

The X-Rel$^1$ is preferably a group as described in U.S. Pat. No. 4,248,962 that enables release of $T^1$-INH from X-Rel$^1$ by means of intramolecular displacement and $T^1$ is preferably a group as described in U.S. Pat. Nos. 4,409,323 and 4,959,299 that enables release of INH from $T^1$ by means of an electron transfer, preferably by an ethylenic conjugated chain.

A typical coupler (A) of Class 1 of the Invention is a naphtholic coupler represented by the formula:

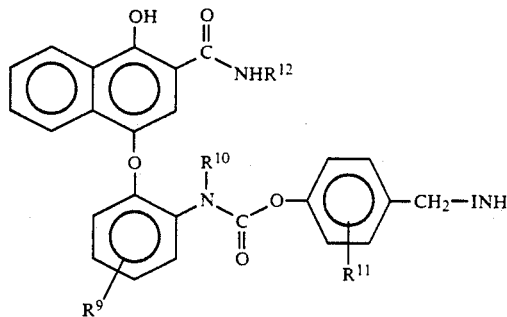

wherein;
$R^9$ is selected from a photographic ballast and a substituent which does not substantially delay release of $T^1$-INH;
$R^{10}$ is selected from substituted and unsubstituted alkyl containing 1 to 3 carbon atoms and a photographic ballast; and
$R^{11}$ is nitro. Other groups which may be considered in place of nitro are hydrogen, amino, carboxylic acid, sulfonic acid, methoxy, chloro, bromo, ester groups such as $-CO_2CH_3$, keto groups such as $COCH_3$, or $-NHCOCH_3$, $-CONHCH_3$, $-NHSO_2CH_3$, $-SO_2NHCH_3$, or $R^{11}$, in combination with the timing group $T^1$, can constitute a substituted or unsubstituted pyridyl moiety.
$R^{12}$ is hydrogen, $CH_3$, methoxyphenyl, hydroxyethoxyphenyl, carboxyphenyl, $-CH_2CO_2CH_3$, $-CH_2CH_2COOH$ or $-CH_2OCH_2CH_2COOH$; and
INH is a heterocyclic development inhibitor group.

An especially preferred naphtholic coupler is represented by the structures I-1 through I-12, of table 1.

Class 2

In the second invention a photographic element as noted, is provided comprising a support bearing at least one photographic silver halide emulsion layer and at least one coupler (A) having a water solubilizing group wherein coupler (A) is capable of forming a compound that is washed out of the photographic element during photographic processing. Coupler (A) has a coupling-off group represented by the formula:

$$-X-REL^2-T^2-INH$$

wherein;
X is selected from oxygen, nitrogen or sulfur
X-Rel$^2$ contains a photographic ballast and is a releasing group for releasing $T^2$-INH from X-Rel$^2$ by elimination electron transfer reaction during photographic processing without substantial delay of releasing;
$T^2$ is a timing group that releases INH by elimination electron transfer reaction with timing delay during photographic processing;
INH is a development inhibitor group;

The X-Rel$^2$ as described is any X-Rel$^2$ releasing group which releases $T^2$-INH from X-Rel$^2$ by an elimination electron transfer reaction during photographic processing without substantial delay of releasing. The X-Rel$^2$ as described is not a timing group that delays release of $T^2$-INH. The X-Rel$^2$ can serve as a carrier for a photographic ballast group for the coupler prior to exposure and photographic processing.

A typical X-Rel$^2$ group is represented by the formula:

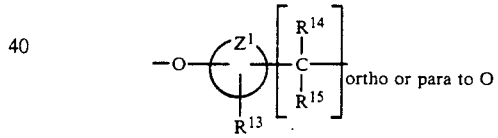 ortho or para to O wherein;
$R^{13}$ is hydrogen or a substituent which does not substantially delay release of $T^2$-INH;
$R^{14}$ and $R^{15}$ is selected from hydrogen, substituted or unsubstituted alkyl, and substituted or unsubstituted aryl;
$Z^1$ represents the atoms necessary to complete a 5 or 6 member aryl or heterocyclic group. At least one of $R^{13}$, $R^{14}$ and $R^{15}$ can be a photographic ballast group.

A substituent which does not substantially delay release of $T^2$-INH and the substituted or unsubstituted alkyl and substituted or unsubstituted aryl, may be selected from nitro, hydrogen, amino, substituted amino, carboxylic acid, sulfonic acid, methoxy, chloro, bromo, ester groups such as $-CO_2CH_3$, keto groups such as $-COCH_3$, or $-NHCOCH_3$, $-CONHCH_3$, $-NHSO_2CH_3$, or $-SO_2NHCH_3$.

The $T^2$ as described is any timing group that releases INH by an elimination electron transfer reaction that enables a time delay between the oxidative coupling of the coupler (A) and the release of INH. The $T^2$ differs from the X-Rel$^2$ in that $T^2$ enables time delay whereas X-Rel$^2$ does not enable substantial time delay.

A typical $T^2$ is represented by the formula:

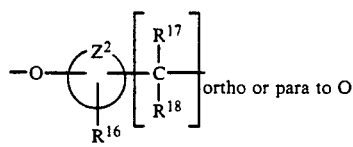

wherein;

$R^{16}$ is hydrogen or a substituent which does not substantially delay release of $T^2$-INH from X-Rel$^2$; $R^{16}$, $R^{17}$, and $R^{18}$ are chosen to provide a minimum time delay of at least 5 seconds.

$R^{17}$ and $R^{18}$ are selected from hydrogen, substituted or unsubstituted alkyl or substituted or unsubstituted aryl and are chosen not to substantially delay release of $T^2$-INH from X-Rel$^2$;

$Z^2$ represents the atoms necessary to complete a 5 or 6 member arylene or heterocyclic group.

A substituent which does

At least one of $R^{26}$, $R^{27}$, $R^{28}$ and $R^{29}$ can be a photographic ballast group;

n is 0, 1 or 2.

A substituent which does not substantially delay release of $T^3$-INH, and the substituted or unsubstituted alkyl and substituted or unsubstituted aryl, may be selected from nitro, hydrogen, amino, substituted amino, carboxylic acid, sulfonic acid, methoxy, chloro, bromo, ester groups such as —$CO_2CH_3$, keto groups such as —$COCH_3$, or —$NHCOCH_3$, —$CONHCH_3$, —$NHSO_2CH_3$, or —$SO_2NHCH_3$.

The $T^3$ as described is any timing group that releases INH by an intramolecular displacement reaction that enables a time delay between the oxidative coupling of the coupler (A) and the release of INH. The $T^3$ differs from the X-Rel$^3$ in that $T^3$ enables time delay whereas X-Rel$^3$ does not enable substantial time delay.

A typical $T^3$ is represented by the formula:

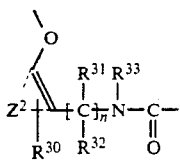

wherein;

$R^{30}$ is hydrogen or a substituent which does not substantially delay release of $T^3$-INH from X-Rel$^3$, $R^{30}$, $R^{31}$, $R^{32}$ and $R^{33}$ are chosen to provide a minimum time delay of at least 5 seconds.

$R^{31}$ and $R^{32}$ is selected from hydrogen, substituted or unsubstituted alkyl or substituted or unsubstituted aryl;

$R^{33}$ is unsubstituted or substituted alkyl or substituted or unsubstituted aryl;

$R^{30}$, $R^{31}$, $R^{32}$ and $R^{33}$ are chosen not to substantially delay release of $T^3$-INH from X-Rel$^3$;

$Z^2$ represents the atoms necessary to complete a 5 or 6 member arylene or heterocyclic group.

n is 0, 1 or 2.

A substituent which does not substantially delay release of $T^3$-INH, and the substituted or unsubstituted alkyl and substituted or unsubstituted aryl, may be selected from nitro, hydrogen, amino, substituted amino, carboxylic acid, sulfonic acid, methoxy, chloro, bromo, ester groups such as —$CO_2CH_3$, keto groups such as —$COCH_3$, or —$NHCOCH_3$, —$CONHCH_3$, —$NHSO_2CH_3$, or —$SO_2NHCH_3$.

The X-Rel$^3$ and $T^3$ are preferably groups as described in U.S. Pat. No. 4,248,962 that enables release of $T^3$-INH from X-Rel$^3$ and INH from $T^3$-INH by means of an intramolecular displacement.

A typical coupler (A) of Class 3 of the Invention is a naphtholic coupler represented by the formula:

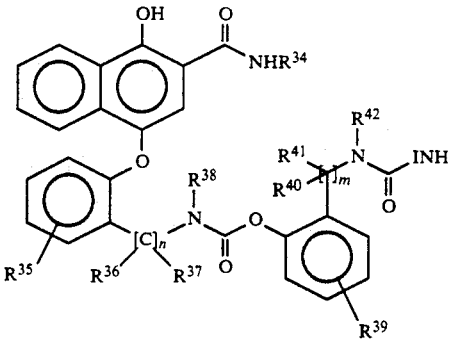

wherein;

$R^{34}$ is hydrogen, $CH_3$, methoxyphenyl, hydroxyethoxyphenyl, carboxyphenyl, —$CH_2CO_2CH_3$, —$CH_2CH_2COOH$ or —$CH_2OCH_2CH_2COOH$;

$R^{35}$ is a photographic ballast, hydrogen, or a substituent which does not substantially delay release of $T^3$-INH from X-Rel$^3$;

$R^{36}$ and $R^{37}$ is selected from hydrogen, substituted and unsubstituted alkyl containing 1 to 3 carbon atoms, or substituted or unsubstituted aryl, and a photographic ballast;

$R^{38}$ is selected from substituted and unsubstituted alkyl containing 1 to 3 carbon atoms, or substituted or unsubstituted aryl, and a photographic ballast;

$R^{39}$ is nitro. Other groups which may be considered in place of nitro are hydrogen, amino, carboxylic acid, sulfonic acid, methoxy, chloro, bromo, ester groups such as —$CO_2CH_3$, keto groups such as —$COCH_3$, or —$NHCOCH_3$, —$CONHCH_3$, —$NHSO_2CH_3$, —$SO_2NHCH_3$, or $R^{39}$, in combination with the timing group $T^3$, can constitute a substituted or unsubstituted pyridyl moiety;

$R^{40}$ and $R^{41}$ is selected from hydrogen, substituted and unsubstituted alkyl containing 1 to 3 carbon atoms, or substituted or unsubstituted aryl;

$R^{42}$ is selected from substituted and unsubstituted alkyl containing 1 to 3 carbon atoms, or substituted or unsubstituted aryl;

n and m are individually 0, 1 or 2.

A substituent which does not substantially delay release of $T^3$-INH, and the substituted or unsubstituted alkyl and substituted or unsubstituted aryl, may be selected from nitro, hydrogen, amino, substituted amino, carboxylic acid, sulfonic acid, methoxy, chloro, bromo, ester groups such as —$CO_2CH_3$, keto groups such as —$COCH_3$, or —$NHCOCH_3$, —$CONHCH_3$, —$NHSO_2CH_3$, or —$SO_2NHCH_3$.

INH is a heterocyclic development inhibitor group.

An especially preferred naphtholic coupler is represented by the structures I-17 through I-21, of table 3. While the invention has been described with respect to naphtholic couplers, it has application to other couplers such as yellow, or magenta dye forming couplers.

Class 4

In the fourth invention a photographic element as noted, is provided comprising a support bearing at least one photographic silver halide emulsion layer and at least one coupler (A) having a water solubilizing group wherein coupler (A) is capable of forming a compound that is washed out of the photographic element during photographic processing. Coupler (A) has a coupling-off group represented by the formula:

$$-X-REL^4-T^4-INH$$

wherein;

X is selected from oxygen, nitrogen or sulfur

X-Rel$^4$ is a releasing group for releasing T$^4$-INH from X-Rel$^4$ by elimination electron transfer reaction during photographic processing without substantial delay of releasing;

T$^4$ is a timing group that releases INH by intramolecular displacement reaction with timing delay during photographic processing;

INH is a development inhibitor group.

The X-Rel$^4$ as described is any X-Rel$^4$ releasing group which releases T$^4$-INH from X-Rel$^4$ by an elimination electron transfer reaction during photographic processing without substantial delay of releasing. The X-Rel$^4$ as described is not a timing group that delays release of T$^4$-INH. The X-Rel$^4$ can serve as a carrier for a photographic ballast group for the coupler prior to exposure and photographic processing.

A typical X-Rel$^4$ group is represented by the formula:

$$-O-\left(Z^1\right)\left[\begin{array}{c}R^{44}\\|\\C\\|\\R^{45}\end{array}\right]_{R^{43}} \text{ortho or para to O}$$

wherein;

R$^{43}$ is hydrogen or a substituent which does not substantially delay release of T$^4$-INH;

R$^{44}$ and R$^{45}$ is selected from hydrogen, substituted or unsubstituted alkyl, and substituted or unsubstituted aryl and are selected not to substantially delay release of T$^4$-INH;

R$^{43}$, R$^{44}$ and R$^{45}$ can be a photographic ballast and are selected not to substantially delay release of T$^4$INH; and Z$^1$ represents the atoms necessary to complete a 5 or 6 member aryl or heterocyclic group;

A substituent which does not substantially delay release of T$^4$-INH, and the substituted or unsubstituted alkyl and substituted or unsubstituted aryl, may be selected from nitro, hydrogen, amino, substituted amino, carboxylic acid, sulfonic acid, methoxy, chloro, bromo, ester groups such as —CO$_2$CH$_3$, keto groups such as —COCH$_3$, or —NHCOCH$_3$, —CONHCH$_3$, —NHSO$_2$CH$_3$, or —SO$_2$NHCH$_3$.

The T$^4$ as described is any timing group that releases INH by an intramolecular displacement reaction that enables a time delay between the oxidative coupling of the coupler (A) and the release of INH. The T$^4$ differs from the X-Rel$^4$ in that T$^4$ enables time delay whereas X-Rel$^4$ does not enable substantial time delay.

A typical T$^4$ is represented by the formula:

$$Z^2 + \left(\begin{array}{c}R^{47}\\|\\C\\|\\R^{48}\end{array}\right)_n \begin{array}{c}R^{49}\\|\\N-C-\\||\\O\end{array}$$

wherein

Z$^2$ represents the atoms necessary to complete a 5 or 6 member arylene or heterocyclic group;

R$^{46}$ is hydrogen or a substituent which does not substantially delay release of T$^4$-INH from X-Rel$^4$;

R$^{47}$ and R$^{48}$ are selected from hydrogen, substituted or unsubstituted alkyl or substituted or unsubstituted aryl;

R$^{49}$ is unsubstituted or substituted alkyl or substituted or unsubstituted aryl;

R$^{46}$, R$^{47}$, R$^{48}$ and R$^{49}$ are chosen to provide a minimum time delay of at least 5 seconds; and n is 0, 1, or 2.

A substituent which does not substantially delay release of T$^4$-INH, and the substituted or unsubstituted alkyl and substituted or unsubstituted aryl, may be selected from nitro, hydrogen, amino, substituted amino, carboxylic acid, sulfonic acid, methoxy, chloro, bromo, ester groups such as —CO$_2$CH$_3$, keto groups such as —COCH$_3$, or —NHCOCH$_3$, —CONHCH$_3$, —NHSO$_2$CH$_3$, or —SO$_2$NHCH$_3$.

The X-Rel$^4$ is preferably a group as described in U.S. Pat. Nos. 4,409,323 and 4,959,299, that enables release of T$^4$-INH from X-Rel$^4$ by means of electron transfer and T$^4$ is preferably a group as described in U.S. Pat. No. 4,248,962 that enables release of INH from T$^4$ by means of intramolecular displacement.

A typical coupler (A) of Class 4 of the Invention is a naphtholic coupler represented by the formula:

wherein;

R$^{50}$ is hydrogen, CH$_3$, methoxyphenyl, hydroxyethoxyphenyl, carboxyphenyl, —CH$_2$CO$_2$CH$_3$, —CH$_2$CH$_2$COOH or —CH$_2$OCH$_2$CH$_2$COOH;

R$^{51}$ is hydrogen, or a substituent which does not substantially delay release of T$^4$-INH from X-Rel$^4$;

R$^{52}$ and R$^{53}$ is selected from hydrogen, substituted and unsubstituted alkyl, or substituted or unsubstituted aryl;

R$^{54}$ is nitro. Other groups which may be considered in place of nitro are hydrogen, amino, carboxylic acid, sulfonic acid, methoxy, chloro, bromo, ester groups such as —CO$_2$CH$_3$, keto groups such as —COCH$_3$, or —NHCOCH$_3$, —CONHCH$_3$, —NHSO$_2$CH$_3$, —SO$_2$NHCH$_3$, or R$^{54}$, in combination with the timing group T$^4$, can constitute a substituted or unsubstituted pyridyl moiety;

R$^{55}$ and R$^{56}$ is selected from hydrogen, substituted and unsubstituted alkyl, or substituted or unsubstituted aryl;

R$^{57}$ is selected from substituted and unsubstituted alkyl containing 1 to 3 carbon atoms or substituted or unsubstituted aryl;

R$^{51}$, R$^{52}$ or R$^{53}$ contains a photographic ballast;

R$^{51}$, R$^{52}$, R$^{53}$, R$^{54}$, R$^{55}$, R$^{56}$ and R$^{57}$ are selected as not to substantially delay release of T$^4$-INH from X-Rel$^4$;

n and m are individually 0, 1, or 2; and

INH is a heterocyclic development inhibitor group.

An especially preferred naphtholic coupler is represented by the structures I-22 through I-25, of table 4. While the invention has been described with respect to naphtholic couplers, it has application to other couplers such as yellow, or magenta dye forming couplers.

Delay of release as measured by half-life can extend to, but not beyond the normal period of time required for developing the photographic element. That is, in the present invention at least half of the INH that is coupled off must be released at the end of the developing period. Delay of release of INH is usually not less than about 5 seconds, preferably is in the range of 5 to 600 seconds and typically in the range of 10 to 100 seconds. This can be determined in most cases in an aqueous solution at pH 10 or pH 14.

In the present invention, release of the timing group in the development of a photographic element is without substantial delay. Release of the timing group (as measured by half-life), can occur in not normally greater than 5 seconds, preferably less than 2 to 3 seconds, and typically less than 1 second half-life. As noted, the half-life can be determined in most cases in an aqueous solution at pH 10 or pH 14.

By "aqueous solution at pH 10" is meant an aqueous solution containing 3% Triton X-100, (a nonionic surfactant, available from the Aldrich Chemical Co., Milwaukee, Wis.), at 23° C. and pH adjusted to 10 using phosphate buffer.

By "aqueous solution at pH 14" is meant an solution containing 45% acetonitrile and 55% aqueous 0.1N potassium hydroxide at 23° C.

A coupler moiety to which the coupling-off group is attached is preferably a cyan, magenta or yellow dye-forming coupler moiety. Acetanilide and naphthol couplers are highly preferred.

As used herein the term "coupler" refers to the entire compound, including the coupler moiety (COUP), and the coupling-off group including the INH. The term "coupler moiety" refers to that portion of the compound other than the coupling-off group.

A process of forming an image having the described advantages comprises developing an exposed photographic element by means of a color developing agent in the presence of described coupler (A).

The water solubilizing group (SOL) can be any water solubilizing group known in the photographic art to enable wash-out of the dye formed in photographic processing from the coupler (A). Typical water-solubilizing groups include groups terminated with an acid group, such as carboxy, sulfo or hydroxy which may also form a salt and other groups described in U.S. Pat. No. 4,482,629 (col. 4, lines 1-3). The coupler (A) can have one or more water-solubilizing groups. The number and type of water solubilizing groups should not be sufficient to make the coupler (A) mobile in the photographic element prior to exposure and processing.

A typical water-solubilizing group (SOL) is a carbonamido group -CONHRa wherein Ra is hydrogen, an alkyl group containing 1 to 3 carbon atoms, preferably —CONHCH$_3$ or —CONHC$_2$H$_5$; or a group containing a water solubilizing group, such as carboxy, sulfo or hydroxy groups, for instance, —CONH$_2$CH$_2$CH$_2$OH, —CONH$_2$CH$_2$CO$_2$H, or —CONH$_2$CH$_2$CH$_2$CO$_2$H. Such a group can be, for example, in the 2-position of a naphtholic coupler containing the coupling-off group in the coupling position.

INH can be any releasable development inhibitor group. Typical INH groups are described in, for example U.S. Pat. Nos. 4,477,563; 4,782,012; 4,886,736; 4,912,024; 4,959,299; and 5,026,628; the disclosures of which are incorporated herein by reference. Preferred development inhibitor groups are heterocyclic inhibitor groups which for example, include mercaptoterazoles, mercaptoxadiazoles, mercaptothiadoazoles and benzotriazoles. Structures A-1 through A-8 as follows, represent typical releasable development inhibitor groups.

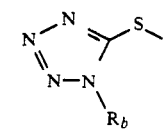

A-1

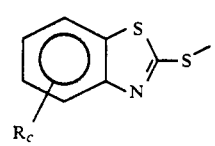

A-2

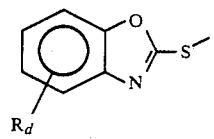

A-3

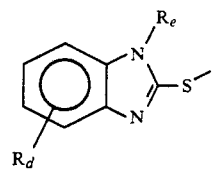

A-4

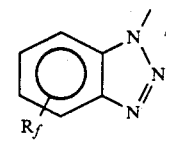

A-5

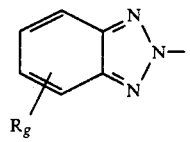

A-6

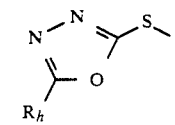

A-7

-continued

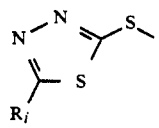
A-8 wherein:

$R_b$, $R_e$, $R_h$, and $R_i$ are individually hydrogen, substituted or unsubstituted alkyl of 1 to 8 carbon atoms such as methyl, ethyl, propyl, butyl, 1-ethylpentyl, 2-ethoxyethyl, substituted phenyl, unsubstituted phenyl; substituted or unsubstituted phenyl of 6 to 10 carbon atoms; alkylthio, such as methyl, ethyl, propyl, butyl or octylthio; or alkyl esters such as $-CO_2CH_3$, $-CO_2C_2H_5$, $-CO_2C_3H_7$, $-CO_2C_4H_9$, $-CH_2CO_2CH_3$, $-CH_2CO_2C_2H_5$, $-CH_2CO_2C_3H_7$, $-CH_2CO_2C_4H_9$, $-CH_2CH_2CO_2CH_3$, $-CH_2CH_2CO_2C_2H_5$, $-CH_2CH_2CO_2C_3H_7$, and $-CH_2CH_2CO_2C_4H_9$; or aryl esters such as $-CO_2Rj$, $-CH_2CO_2R_j$, $-CH_2CH_2CO_2R_j$, wherein $R_j$ is substituted or unsubstituted aryl; wherein:

$R_c$, $R_d$, $R_f$, and $R_g$ are as described for $R_b$, $R_e$, $R_h$, and $R_i$; or, are individually one or more halogen such as chloro, fluoro, or bromo; carboxyl, esters or other substituents such as $-NHCOCH_3$, $-SO_2OCH_3$, $-OCH_2CH_2SO_2CH_3$, $-OCOCH_2CH_3$, $-NHCOCH_3$ or nitro groups.

As used herein the term photographic ballast group (BALL) is a ballast group that is known in the photographic art. The ballast group as described is an organic group of such size and configuration as to confer on the molecule sufficient bulk to render the molecule substantially non-diffusible from the layer in which it is coated in a photographic element. Representative ballast groups include substituted or unsubstituted alkyl or aryl groups typically containing 8 to 40 carbon atoms. The ballast group as described, is located on X-Rel[1] and can be either $R^9$ or $R^{10}$.

A process of forming an image having the described advantages comprises developing an exposed photographic element by means of a color developing agent in the presence of described coupler (A), as described.

A preferred coupler (A) is an acetanilide or naphtholic coupler.

The coupler moiety (COUP) can be any moiety having a water solubilizing group, provided that the coupler moiety will react with oxidized color developing agent to cleave the bond between the X-Rel (RELEASING GROUP) portion of the coupling-off group and the coupler moiety. The coupler moiety herein includes coupler moieties employed in conventional color-forming couplers that yield colorless products on reaction with oxidized color developing agents as well as coupler moieties that yield colored products on reaction with oxidized color developing agents. Both types of coupler moieties are known to those skilled in the photographic art.

The coupler moiety can be ballasted or unballasted provided that the dye formed upon oxidative coupling is capable of being washed out of the photographic element. It can be monomeric, or it can be part of a dimeric, oligomeric or polymeric coupler, in which case more that one group containing PUG can be contained in the coupler, or it can form part of a bis compound in which the INH forms part of a link between two coupler moieties.

The INH can be any of the mentioned heterocyclic inhibitor groups that is typically made available in a photographic element in an imagewise fashion. Combinations of couplers, such as combinations of couplers (A), are also useful. Combinations of at least one coupler (A) with other couplers that are capable of releasing a reagent or a photographic dye are useful. A photographic reagent herein is a moiety that upon release further reacts with components in the photographic element, such as development inhibitor, a development accelerator, a bleach inhibitor, a bleach accelerator, a coupler (for example, a competing coupler, a dye-forming coupler, or a development inhibitor releasing coupler (DIR coupler)), a dye precursor, a dye, a developing agent (for example, a competing developing agent, a dye-forming developing agent, or a silver halide developing agent), a silver complexing agent, a fixing agent, an image toner, a stabilizer, a hardener, a tanning agent, a fogging agent, an ultraviolet radiation absorber, an antifoggant, a nucleator, a chemical or spectral sensitizer or a desensitizer.

The INH can be present in the coupling-off group as a preformed species or it can be present in a blocked form or as a precursor.

There follows a listing of patents and publications that describe representative couplers that are useful with couplers of the invention and coupler moieties useful in the coupler (A) of the invention:

I. COUP's

A. Couplers which form cyan dyes upon reaction with oxidized color developing agents are described in such representative patents and publications as: U.S. Pat. Nos. 2,772,162; 2,895,826; 3,002,836; 3,034,892; 2,474,293; 2,423,730; 2,367,531; 3,041,236; 4,333,999 and "Farbkuppler-eine Literaturubersicht," published in Agfa Mitteilungen, Band III, pp. 156-175 (1961).

Preferably such couplers are phenols and naphthols which form cyan dyes on reaction with oxidized color developing agent.

B. Couplers which form magenta dyes upon reaction with oxidized color developing agent are publications as: U.S. Pat. Nos. 2,600,788; 2,369,489; 2,343,703; 2,311,082; 3,152,896; 3,519,429; 3,062,653; 2,908,573 and "Farbkuppler-eine Mitteilungen, Band III, pp. 126-156 (1961).

Preferably such magenta dye-forming couplers are pyrazolones or pyrazolotriazole couplers.

C. Couplers which form yellow dyes upon reaction with oxidized and color developing agent are described in such representative patents and publications as: U.S. Pat. Nos. 2,875,057; 2,407,210; 3,265,506; 2,298,443; 3,048,194; 3,447,928 and "Farbkuppler-eine Mitteilungen, Band III, pp. 112-126 (1961).

Preferably such yellow dye-forming couplers are acylacetamides, such as benzoylacetamides and pivaloylacetamides.

D. Couplers which form colorless products upon reaction with oxidized color developing agent are described in such representative patents as: U.K. Pat. No. 861,138; U.S. Pat. Nos. 3,632,345; 3,928,041; 3,958,993 and 3,961,959.

The photographic couplers of the invention can be incorporated in photographic elements by means and processes known in the photographic art. In a photographic element prior to exposure and processing the photographic coupler should be of such size and configuration that it will not diffuse through the photographic layers.

Photographic elements of this invention can be processed by conventional techniques in which color forming couplers and color developing agents are incorporated in separate processing solutions or compositions or in the element.

Photographic elements in which the couplers of this invention are incorporated can be a simple element comprising a support and a single silver halide emulsion layer or they can be multilayer, multicolor elements. The couplers of this invention can be incorporated in at least one of the silver halide emulsion layers and/or in at least one other layer, such as an adjacent layer, where they will come into reactive association with oxidized color developing agent which has developed silver halide in the emulsion layer. The silver halide emulsion layer can contain or have associated with it, other photographic coupler compounds, such as dye-forming couplers, colored masking couplers, and/or competing couplers. These other photographic couplers can form dyes of the same or different color and hue as the photographic couplers of this invention. Additionally, the silver halide emulsion layers and other layers of the photographic element can contain addenda conventionally contained in such layers.

A typical multilayer, multicolor photographic element can comprise a support having thereon a red-sensitive silver halide emulsion unit having associated therewith a cyan dye image-providing material, a green-sensitive silver halide emulsion unit having associated therewith a magenta dye image-providing material and a blue-sensitive silver halide emulsion unit having associated therewith a yellow dye image-providing material, at least one of the silver halide emulsion units having associated there with a photographic coupler of the invention. Each silver halide emulsion unit can be composed of one or more layers and the various units and layers can be arranged in different locations with respect to one another.

The couplers of this invention can be incorporated in or associated with one or more layers or units of the photographic element. For example, a layer or unit affected by PUG can be controlled by incorporating in appropriate locations in the element a scavenger layer which will confine the action of PUG to the desired layer or unit. At least one of the layers of the photographic element can be, for example, a mordant layer or a barrier layer.

The light sensitive silver halide emulsions can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide and mixtures thereof. The emulsions can be negative-working or direct-positive emulsions. They can form, latent images predominantly on the surface of the silver halide grains or predominantly on the interior of the silver halide grains. They can be chemically and spectrally sensitized. The emulsions typically will be gelatin emulsions although other hydrophilic colloids are useful. Tabular grain light sensitive silver halides are particularly useful such as described in *Research Disclosure*, January 1983, Item No. 22534, and U.S. Pat. No. 4,434,226.

The support can be any support used with photographic elements. Typical supports include cellulose nitrate film, cellulose acetate film, polyvinylacetal film, polyethylene terephthalate film, polycarbonate film and related films or resinous materials as well as glass, paper, metal and the like. Typically, a flexible support is employed, such as a polymeric film or paper support. Paper supports can be acetylated or coated with baryta and/or an α-olefin polymer, particularly a polymer of an α-olefin containing 2 to 10 carbon atoms such as polyethylene, polypropylene, ethylene-butene copolymers and the like.

The coupler (A) can be used in photographic elements in the same way as photographic couplers which release mercaptotetrazole inhibitor groups have previously been used in photographic elements. However, because of the improved ability to control the release of the INH the couplers permit enhanced effects or more selective effects.

In the following discussion of suitable materials for use in the emulsions and elements of this invention, reference will be made to *Research Disclosure*, December 1978, Item 17643, published by Industrial Opportunities Ltd., Homewell Havant, Hampshire, P09 1EF, U.K., the disclosures of which are incorporated herein by reference. This publication will be identified hereafter by the term "Research Disclosure".

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents useful in the invention are p-phenylene diamines. Especially preferred are 4-amino-N,N-diethylaniline hydrochloride; 4-amino-3-methyl-N,N-diethylaniline hydrochloride; 4-amino-3-methyl-N-ethyl-N-β(methanesulfonamido)ethylaniline sulfate hydrate; 4-amino-3-methyl-N-ethyl-N-β-hydroxyethylaniline sulfate; 4-amino-3-β-(methanesulfonamido)-ethyl-N,N-diethlaniline hydrochloride; and 4-amino-N-ethyl-N-(2-methoxyethyl)-m-toluidine di-p-toluenesulfonic acid.

The described photographic materials and processes can be used with photographic silver halide emulsions and addenda known to be useful in the photographic art, as described in, for example, *Research Disclosure*, December 1989, Item No. 308,119, the disclosures of which are incorporated herein by reference.

With negative working silver halide the processing step described above gives a negative image. To obtain a positive (or reversal) image, this step can be preceded by development with a non-chromogenic developing agent to develop exposed silver halide, but not form a dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

Representative compounds of the invention can be prepared as follows:

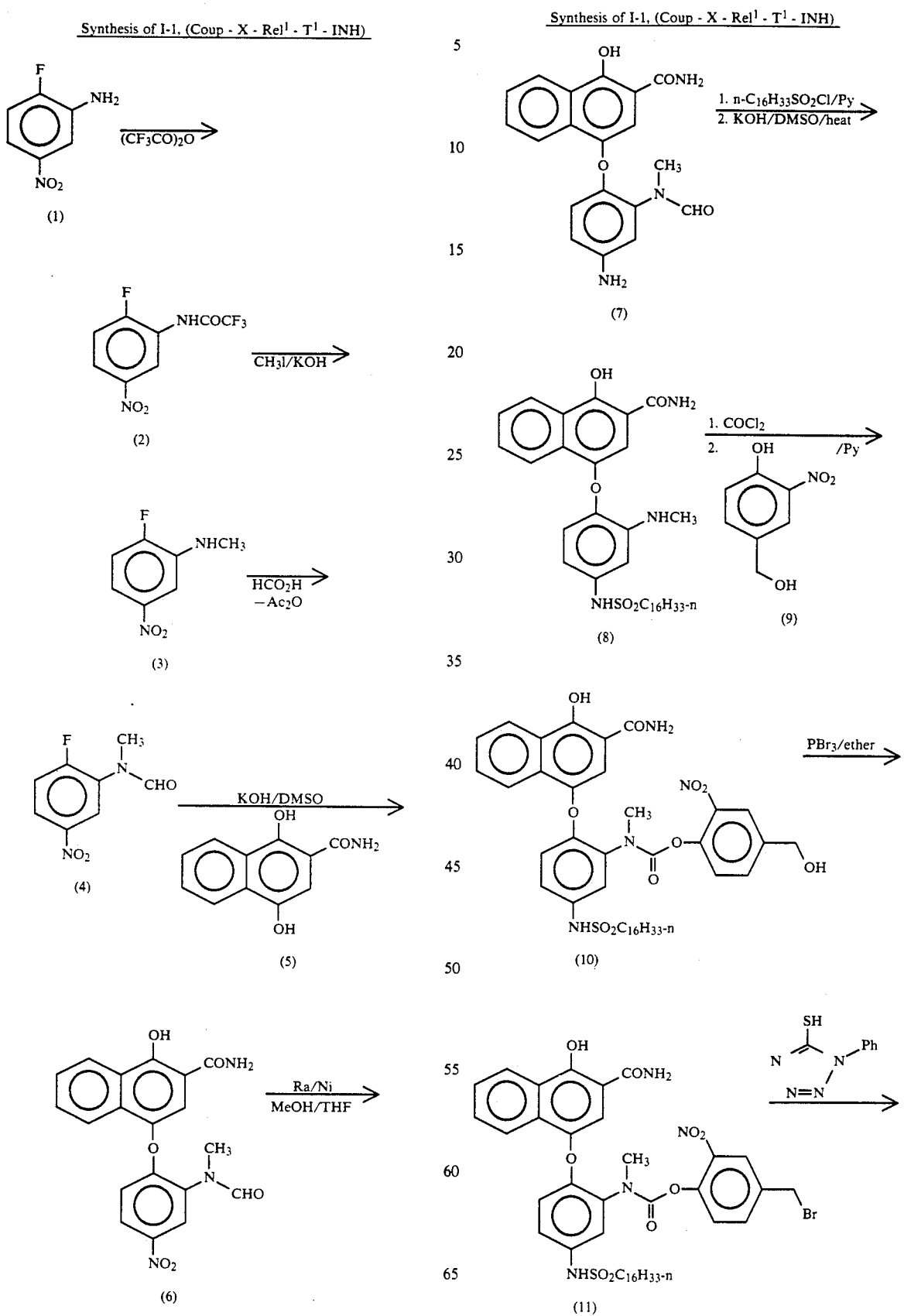

-continued
Synthesis of I-1, (Coup - X - Rel¹ - T¹ - INH)

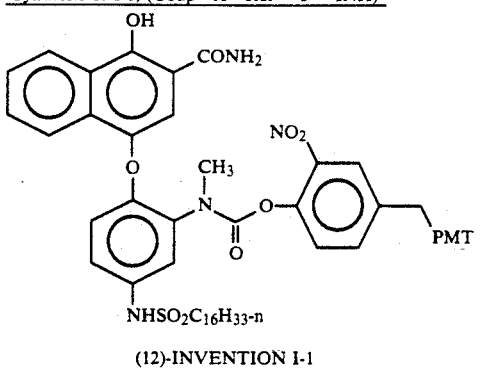

(12)-INVENTION I-1

Compound (2)

2-fluoro-5-nitroaniline (75 g, 0.48 Mole), (1) was taken up in THF (750 mL). This solution was cooled to 0° C. and trifluoroacetic anhydride (130 mL, 0.933Mole), was added fairly rapidly over a 30 minute period. At the end of the addition the yellow color of the amine had changed to give an orange solution. The reaction was stirred at room temperature for 8 hours. At the end of this period the solvent was removed under reduced pressure, the residue coevaporated with toluene, and the solid recrystallized from toluene. The product, compound (2), was collected as an off white solid, 106 g (88%).

Compound (3)

Compound (2), (103.5 g, 0.41 Mole) was taken up in acetone (500 mL). To this solution was added methyl iodide (187.6 g, 1.32 Mole) with stirring, followed by 85%-KOH, (94 g, 1.68 Mole). Stirring at room temperature was continued wherein the solution began to reflux. After about 30-45 minutes the refluxing subsided and the temperature began to fall. Stirring was continued for about 1.5 hours. At the end of this period the precipitated KI was filtered off and the filtrate concentrated under reduced pressure. The residue so obtained was taken up in an ethyl acetate water mix, separated, and the ethyl acetate layer washed with water ($\times 3$). The original layer was then dried (MgSO$_4$), filtered, and the solvent removed under reduced pressure. The crystals so obtained were washed out of the flask with heptane. The product compound (3), amounted to 122.5 g, (88%).

Compound (4)

The mixed anhydride, prepared from acetic anhydride (8.3 mL) and formic acid (4.2 mL) at 0° C. over a 1 hour period, was added dropwise to compound (3), (6.6 g, 38.76 mMole) in THF (50 mL) at 0° C. The temperature of the reaction was allowed to reach room temperature and the solution stirred for 2 hours. At the end of this period the solution was concentrated to an oil under reduced pressure and taken up in ethyl acetate. The ethyl acetate was then washed with 2.5% Na2CO5 ($\times 3$), 2N-HCl ($\times 1$), dried, (MgSO$_4$), filtered and the solution concentrated to an oil which slowly crystallized. Yield of compound (4), 5.0 g (65 %).

Compound (6)

1,4-dihydroxy-naphthalene-2-carboxamide, (5), (4.66 g, 22.94 mMole) was dissolved in deoxygenated 10% aqueous DMSO (60 mL) and the solution stirred under a nitrogen atmosphere. To this solution was then added 85%-KOH (3.3 g, 50.08 mMole). The mixture was stirred for approximately 15 minutes at room temperature to get complete dissolution. This solution was then cooled to 5° C. and compound (4), (5.0 g, 25.23 mMole) added all at once as a solid. Stirring was continued while the temperature rose to approximately 10° C. After maintaining the temperature in the range of 5°-10° C. for 15 minutes the reaction mixture was then poured into ice cold 2N-HCl, filtered, washed with water and finally air dried. This gave compound (6), yield 8.5 g, (97%), in sufficient purity to be used in the next step. Compound (7)

Compound (6), (8.5 g, 22.29 mMole) was taken up in THF (50 mL) and methyl alcohol (150 mL) added. Raney-Nickel catalyst which had been prewashed with water ($\times 3$) and methyl alcohol ($\times 3$) was then added to the solution and hydrogenation carried out at room temperature at 50 psi. During the hydrogenation the product crystallizes out but can be redissolved by the addition of more THF. After several hours, when hydrogen up take had ceased, the catalyst was carefully filtered off washing the residue with hot pyridine. On concentrating, the product, compound (7), crystallized out and was filtered off. Yield 7.83 g (100%).

Compound (8)

Compound (7), (7.83 g, 22.29 mMole) was dissolved in dry pyridine (100 mL) and n-hexadecylsulphonyl chloride (7.97 g, 24.52 mMole) added. After stirring the resulting solution for about 30 minutes a further batch of the n-hexadecylsulphonyl chloride (1.0 g) was added. After a further 30 minutes the pyridine was concentrated under reduced pressure and the oily residue taken up in ethyl acetate which was washed with 2N-HCl ($\times 3$), dried, (MgSO$_4$), filtered and concentrated to an oil. When treated with acetonitrile the formamide of compound (8) crystallized out, was filtered off and air dried to yield 9.5 g (67%). The above formamide (8.0 g, 12.50 mMole) was dissolved in DMSO (20 mL) to which was added 85%-KOH (8.24 g, 12.48 mMole) in water (20 mL). The resulting solution was heated on a steam bath for approximately 5 hours. At the end of this period, the reaction solution was cooled, poured into 2N-HCl and extracted with ethyl acetate. The ethyl acetate extracts were then washed with 2N-HCl ($\times 1$), dried, (MgSO$_4$), filtered, and concentrated under reduced pressure. The product crystallized out before dryness, it was filtered off washed with a little cold ethyl acetate and air dried. The product, compound (8), was obtained as an off white solid, yield 4.7 g (62%).

Compound (10)

Compound (8), (6.5 g, 10.62 mMole) was dissolved in THF (50 mL) and a 12% solution of phosgene in toluene (26 mL, 31.87 mMole) added followed by N,N-diethylaniline (1.14 mL, 7.19 mMole). After stirring at room temperature for 15 minutes the solvent was removed under reduced pressure to give the crude carbamyl chloride of compound (8). This carbamyl chloride was then used as such in the next step. 5 The above crude carbamyl chloride was dissolved in dry pyridine (60 mL) and 4-hydroxymethyl-2-nitrophenol (9), (1.97 g, 11.68 mMole) added and the resulting solution stirred at room temperature for 3 hours. The solution was then concentrated under reduced pressure and the oil taken up in ethyl acetate, washed with 2N-HCl, ($\times 3$), dried, (MgSO$_4$), filtered, and once again concentrated to an oil. This oil was dissolved in a mixture of ethyl acetate (50%), dichloromethane (10%) and heptane (40%) and pressure chromtographed over silica gel eluting with the same solvent mixture. The major band was collected to yield compound (10), 7.5 g, (88%).

Compound (11)

Compound (10), (7.0 g, 8.67 mMole) was dissolved in dry ether (100 mL) and phosphorus tribromide (0.9 mL, 9.54 mMole) in ether (10 mL) was added dropwise. After the addition a solid had precipitated which was dissolved by the addition of THF (20 mL). After stirring the reaction solution at room temperature for 30 minutes it was concentrated and the oil taken up in ethyl acetate. The ethyl acetate solution was then washed with 2N-HCl (×1), dried, (MgSO4), and taken to an oil once again. This oil, compound (11) was used such in the next step.

Compound (12) - INVENTION I-1

The crude compound (11), (9.29 mMole) was dissolved in dry DMF (60 mL) and NaPMT (2.05 g, 10.22 mMole) added. After stirring this solution at room temperature for 1 hour, it was poured into 2N-HCl and extracted with ethyl acetate (×3). The ethyl acetate extracts were combined, washed with 2N-HCl (×3), 2.5%-Na2CO3, (×1), 2N-HCl (×1), dried, (MgSO4), filtered and concentrated to an oil. The oil was taken up in a solvent mixture of ethyl acetate (30%), dichloromethane (10%) and heptane (60%) and pressure chromtographed over silica gel eluting with this solvent mixture of 30:10:60 and then changed to 40:10:50 to collect the major band. Compound (12) - Invention I-1, was collected as a white solid, yield 7.0 g (78%). Calculated for $C_{49}H_{58}N_8O_9S_2$: %C 60.85, %H 6.04, %N 11.59 and %S 6.63 Found: %C 60.74, %H 6.01, %N 11.18 and %S 6.78

Synthesis of I-13, (Coup - X - Rel$^2$ - T$^2$ - INH)

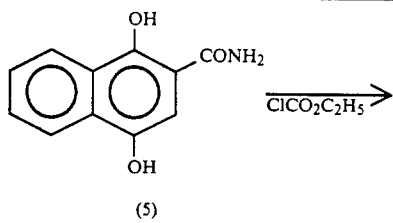

(5)

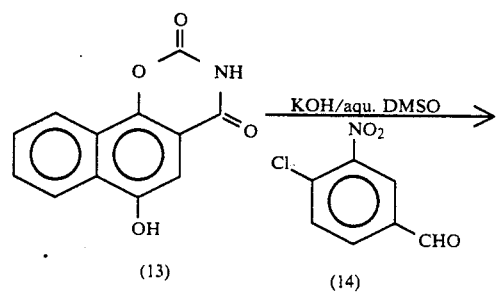

(13)  (14)

-continued
Synthesis of I-13, (Coup - X - Rel$^2$ - T$^2$ - INH)

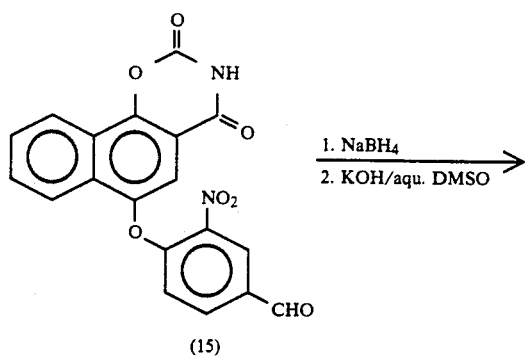

(15)

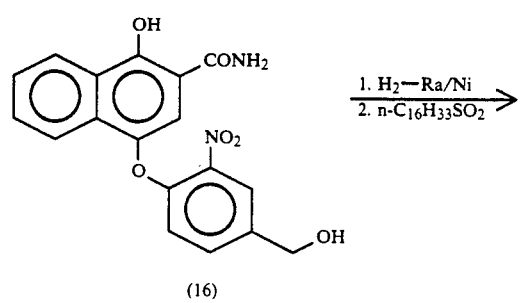

(16)

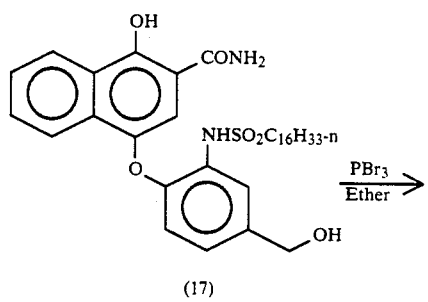

(17)

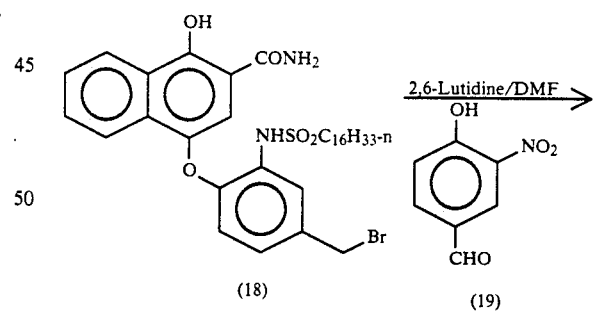

(18)  (19)

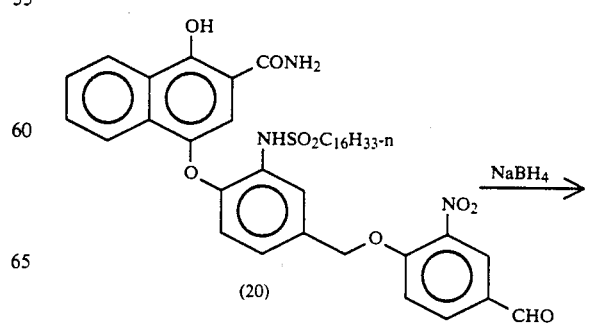

(20)

-continued
Synthesis of I-13, (Coup - X - Rel² - T² - INH)

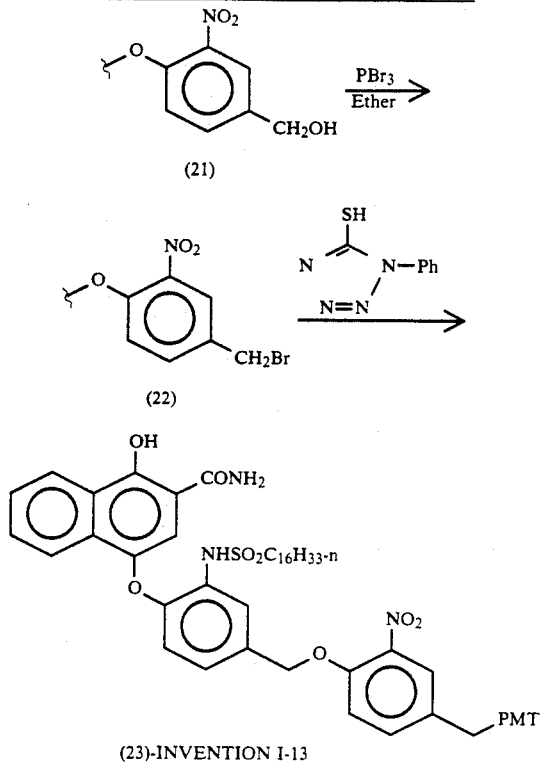

(23)-INVENTION I-13

Compound (5)

Phenyl 1,4-dihydroxy-2-naphthoate (100 g, 356.78 mMole) was dissolved in deoxygenated tetrahydrofuran, (500 mL) and deoxygenated methanol, (500 mL) added. To this solution, stirred at room temperature under a nitrogen atmosphere, was added ammonium acetate, (50,0 g, 648.63 mMole) followed by concentrated ammonium hydroxide, (1.0L). After stirring for 3 hours the reaction solution was then poured into ice cold 2N-HCl, (4.0 L) and enough concentrated HCl added to bring the pH to 1. The resulting product, compound (5), was filtered off, washed well with water and air dried. This material was washed with dichloromethane and air dried again. Yield 62.0 g, (72%).

Compound (13)

Compound (5), (50.0 g, 0.246 mMole) was dissolved in dry pyridine, (150 mL) and acetonitrile, (75 mL) added. The solution was stirred and cooled to −5°-0° C. Ethyl chloroformate, (50 mL, 0.523 mMole) was then added dropwise with stirring while maintaining the temperature at 0° C. After the addition, the cooling bath was removed and the temperature allowed to reach room temperature. The reaction mixture was then gradually heated to reflux and the solvent allowed to distill off. This procedure was continued until the temperature had risen to approximately 120° C. and 150 mL of solvent had been collected. Heating under reflux was continued for an additional 1 hour period. The reaction mixture was then cooled to approximately 50° C. and poured into 2N-HCl (3.0 L) which was maintained at room temperature. The suspension was then stirred for approximately 15 minutes, filtered and the residue washed well with water, acetonitrile and finally ether This gave the product, compound (13), sufficiently pure for the next step. Yield 43.5 g, (77%).

Compound (15)

Compound (13), (23.0 g, 100.35 mMole) was taken up in deoxygenated dimethyl sulphoxide, (250 mL) and deoxygenated water, (25 mL) added. To this solution, stirred at room temperature under nitrogen, was added 85% potassium hydroxide, (9.9 g, 150.53 mMole) and stirring continued until dissolution, approximately 15 minutes. 4-Chloro-3-nitrobenzaldehyde (14), (18.62 g, 100.35 mMole), was then added all at once, and the resulting solution stirred at 60° C. for 1 hour. The reaction mixture was then poured into ice cold 2N-HCl (2.0 L), and filtered off. The product, compound (15), was washed with ether. This product was pure enough to be used in the next step. Yield 28.0 g (74%).

Compound (16)

Compound (15), (28.0 g, 74.01 mMole), in a powdered form, was suspended in tetrahydrofuran, (150 mL) and methanol, (100 mL). Water, (100 mL) was added followed by sodium borohydride, (2.8 g, 74.01 mMole) in small portions. More tetrahydrofuran, (50 mL) was added to aid stirring. At the end of the sodium borohydride addition complete dissolution had been achieved. The reaction was allowed to proceed for a further 15 minutes, then poured into ice cold 2N-HCl (2.0 L), and the product filtered off. The product was washed with methanol and while still wet with solvent, suspended in ethanol and heated to reflux. The solution was cooled, filtered, washed with methanol, ether and finally air dried. A second crop of material was obtained on concentrating the mother liquor. Total yield of the benzyl alcohol precursor to compound (16), 19.5 g, (67%).

The latter compound, (19.0 g, 50 mMole) was suspended in water, (200 mL), containing 85% potassium hydroxide, (26.34 g, 400 mMole). To this mixture was added methanol, (50 mL) and then heated to 80° C. for 1 hour. The resulting dark yellow-brown solution was cooled and poured into ice cold 2N-HCl (2.0 L). The yellow product was filtered off, washed well with water and air dried. Yield of compound (16), 17.7 g (100%).

Compound (17)

Compound (16), (17.7 g, 50 mMOle) was dissolved in tetrahydrofuran, (80 mL) and methanol, (300 mL) added. Raney-Nickel which had been washed several times with water and then methanol, was added and the solution hydrogenated at 55 psi. Hydrogen uptake had ceased after 2 hours. The catalyst was filtered off, washed with methanol and the filtrate concentrated under reduced pressure to give the product. This product, the amino precursor to compound (17), was deemed sufficiently pure to be carried on to the next step. Yield 100%.

The above amino compound, (50.0 mMole) was dissolved in dry pyridine, (150 mL) and n-hexadecylsulphonyl chloride, (16.2 g, 50.0 mMole) added. The solution was stirred at room temperature under a nitrogen atmosphere for 30 minutes. The pyridine was concentrated under reduced pressure and the residue taken up in ethyl acetate. This ethyl acetate solution was then washed with 2N-HCl (×3), dried, (MgSO₄), filtered and concentrated. The residue which resulted crystallized from acetonitrile. After filtering, washing with acetonitrile and drying, the yield of product, compound (17), amounted to 16.3 g, {53% calculated from compound (16)}.

Compound (18)

Compound (17), (4.0 g, 6.53 mMole) was suspended in dry ether, (30 mL) and phosphorous tribromide, (0.68 mL, 7.18 mMole) in ether, (20 mL) added dropwise over a 15 minute period. After the addition the reaction was diluted with ether and the ether solution washed with 2N-HCl (×1), dried, (MgSO$_4$), filtered and concentrated to give compound (18). The yield was 100%.

Compound (20)

Compound (18), (13.5 g, 19.98 mMole) was dissolved in DMF, (100 mL), and 4-hydroxy-3-nitrobenzaldehyde (19), (3.34 g, 19.98 mMole) followed by 2,6-lutidine, (4.64 mL, 40 mMole) were added. The reaction solution was stirred at room temperature for 24 hours. A further batch of base, (4.64 mL), was added and the reaction solution stirred for a further 24 hours. After this period the temperature of the reaction was raised to 60° C. and held there with stirring for a further 24 hours. At the end of this period the reaction was worked up by dilution with ethyl acetate and washing the ethyl acetate layer with 2N-HCl (×2), 2%-Na2CO$_3$ (×3), 2N-HCl (×1), dried (MgSO$_4$), filtered and concentrated under reduced pressure to an oil. This oil was dissolved in a solvent mixture of ethyl acetate (20), dichloromethane (5) and heptane (30), and pressure chromotographed over silica gel eluting with the same solvent mixture. Three major components were collected in the following order of increasing polarity; the formulated derivative of compound (17), the product, compound (20), and the benzyl alcohol compound (17). The yield of compound (20) was 3.4 g, (22%).

Compound (21)

Compound (20), (9.5 g, 12.47 mMole) was dissolved in THF (30 mL), and methyl alcohol (30 mL) added. Sodium borohydride (0.47 g, 12.47 mMole) was gradually added with stirring. After the sodium brohydride had been added the resulting solution was stirred at room temperature for 15 minutes. The reaction solution was then concentrated, taken up in ethyl acetate and the ethyl acetate solution washed with 2N-HCl (×1), dried (MgSO$_4$), filtered and concentrated to an oil under reduced pressure. This oil, compound (21), was used directly in the next step but can be crystallized form ether.

Compound (22)

Compound (21), (12.47 mMole), was dissolved in a 50% solution of THF and ether (100 mL). Phosphorus tribromide (1.2 mL, 12.47 mMole) in ether (20 mL) was then added dropwise. At the end of the addition the reaction solution was stirred at room temperature for 15 minutes. The reaction was then diluted with ethyl acetate, washed with 2N-HCl (×1), brine (×1), dried (MgSO$_4$), filtered and concentrated to an oil. This oil, compound (22), was used directly in the next step of the sequence.

Compound (23) - INVENTION I-13

Compound (22), (12.47 mMole) was dissolved in DMF (60 mL) and NaPMT, (2.5 g, 12.47 mMole) added. The reaction was stirred at room temperature for 15 minutes. It was then diluted with ethyl acetate, washed with 2N-HCl (×1), 2.5% -Na2CO$_3$ (×1), 2N-HCl (×1), brine (×1), dried (MgSO$_4$), filtered and concentrated under reduced pressure to an oil. This oil was dissolved in a solvent mixture of ethyl acetate (15), dichloromethane (5), and heptane (30) and pressure chromotographed over silica gel eluting with the same solvent mixture. Yield of compound (23) - Invention I-13, 9.8 g (85%). Calculated for $C_{48}H_{57}O_8S_2$: %C 62.38, %H 6.22, %N 10.61, %S 6.14 Found: %C 62.15, %H 6.23, %N 10.19, %S 7.21

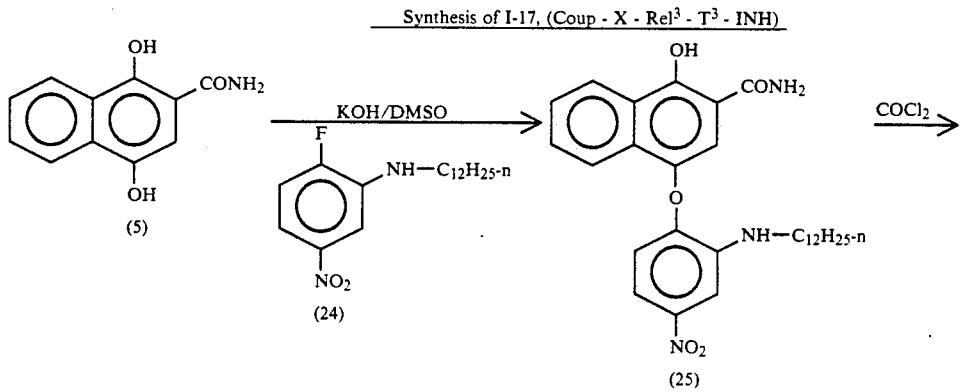

-continued
Synthesis of I-17, (Coup - X - Rel³ - T³ - INH)

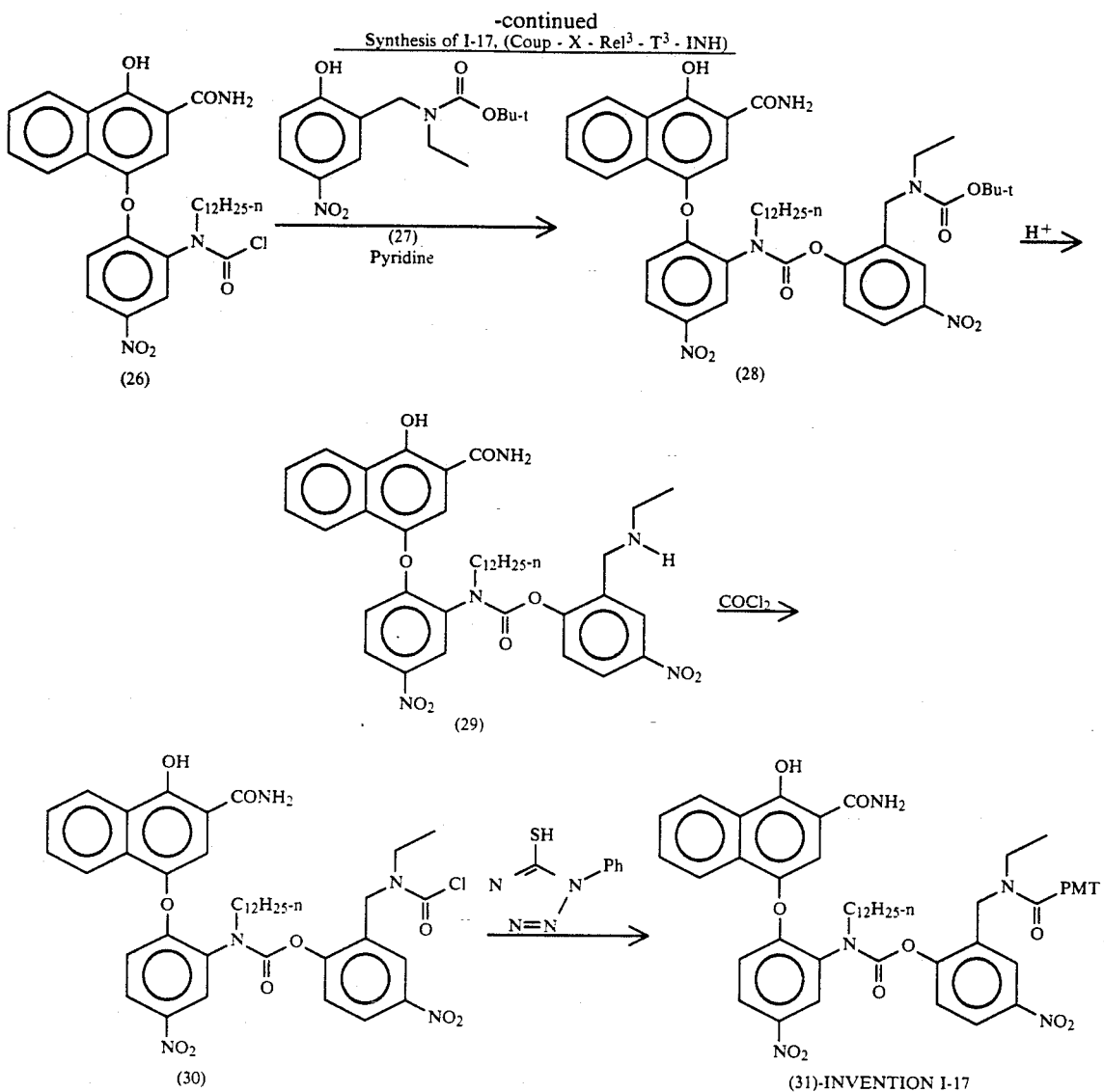

Compound (25)

1,4-Dihydroxynaphthalene-2-carboxamide, (5), (10.0 g, 49.21 mMole) was dissolved in deoxygenated DMSO, (300 mL) containing water (30 mL). To this solution, stirred under nitrogen, was added 85%-KOH (12.2 g, 0.184 Mole) and stirring continued for a further 15 minutes. To the resulting dark coloured solution was added N-dodecyl-2-fluoro-5-nitroaniline, (24), (26.4 g, 0.081 Mole), all at once and the reaction mixture stirred at 600° C. for 2 hours. The reaction was then poured into 2N-HCl, treated with a small volume of ether and the resulting solid filtered off. This solid was washed with methanol, then ether and air dried to give compound (25), 25.0 g, (100%). This product was pure enough to be used in the next step.

Compound (26)

Compound (25), (24.6 g, 48.46 mMole) was dissolved in THF, (300 mL) and phosgene (96 mL of a 15% solution in toluene, 145.38 mMole) added all at once. After stirring at room temperature for 15 minutes the reaction solution was concentrated under reduced pressure. The resulting oil was dissolved in ether and treated with an equal volume of heptane. The yellow solid, compound (26) was filtered off, washed with heptane and air dried to give 22.0 g, (80%).

Compound (27)

2-(N-ethyl)aminomethyl-4-nitrophenol (95.9 g, 0.412 Mole), was suspended with stirring, in acetonitrile (800 mL) and triethylamine (168.5 mL, 1.22 Mole), gradually added. To this solution was then gradually added di-t-butyl dicarbonate (100.0 g, 0.458 Mole). The mixture was then heated under gentle reflux for 18 hours. At the end of this period the reaction solution was cooled, poured into cold 2N-HCl (3.0 L), and the tan solid filtered off. The product, compound (27), was washed well with water and air dried to give a 100% yield of product of sufficient purity to be used in the next step.

Compound (28)

Compound (26), (16.2 g, 28.42 mMole) was dissolved in dry pyridine (100 mL) and compound (27), (9.3 g, 31.26 mMole) added with stirring followed by triethylamine (4 mL, 0 28.42 mMole). The resulting dark yellow coloured solution was stirred at room temperature under a nitrogen atmosphere for 12 hours. The reaction solution was then concentrated under reduced pressure and the residue taken up in ethyl acetate. The ethyl acetate solution was washed with 2N-HCl (×2), dried (MgSO$_4$), filtered and concentrated under reduced pressure to an oil. This oil was dissolved in 20% ethyl acetate in heptane and passed through a pad of silica gel eluting with the same solvent mixture to remove traces of impurities and the product then eluted from the silica gel with 30% ethyl acetate. The product compound (28), was isolated as a yellow foam. Yield 23 g, (97%).

Compound (29)

Compound (28) (4.5 g, 5.42 mMole), was dissolved in dichloromethane (30 mL) and trifluoroacetic acid (20 mL) added. The reaction solution was then stirred at room temperature for 60 minutes. After this time the solution was concentrated and dissolved in ethyl acetate. The ethyl acetate solution was then washed with water (×3), dried (MgSO$_4$), filtered and concentrated to an oil. This oil, compound (29), was used as such in the next step.

Compound (30)

Compound (29) (5.42 mMole), as described above, was dissolved in THF (50 mL) and phosgene (8 mLs of a 20% solution in toluene, 16.26 mMole) was added and the reaction mixture stirred at room temperature for 60 minutes. At the end of this time the reaction solution was concentrated under reduced pressure to give compound (30). This product was used as such in the next step.

Compound (31) - Invention I-17

Compound (30) (5.42 mMole), as described above, was dissolved in dry pyridine (20 mL) and the sodium salt of phenyl mercaptotetrazole (1.2 g, 5.96 mMole) added. The resulting solution was stirred at room temperature for 1 hour. At the end of this time the reaction solution was diluted with ethyl acetate, and the ethyl acetate solution washed with 2N-HCl (×1), 2.5%-Na$_2$CO$_3$ (×2), 2N-HCl (×1), dried (MgSO$_4$), filtered and concentrated to an oil under reduced pressure. The oil was dissolved in 40% ethyl acetate in heptane and pressure chromatographed eluting with 30% ethyl acetate in heptane to give the product, compound (31) - Invention I-17. Yield 3.2 g, {63% from compound (28)}. m/z: By FDMS molecular ion at 933.

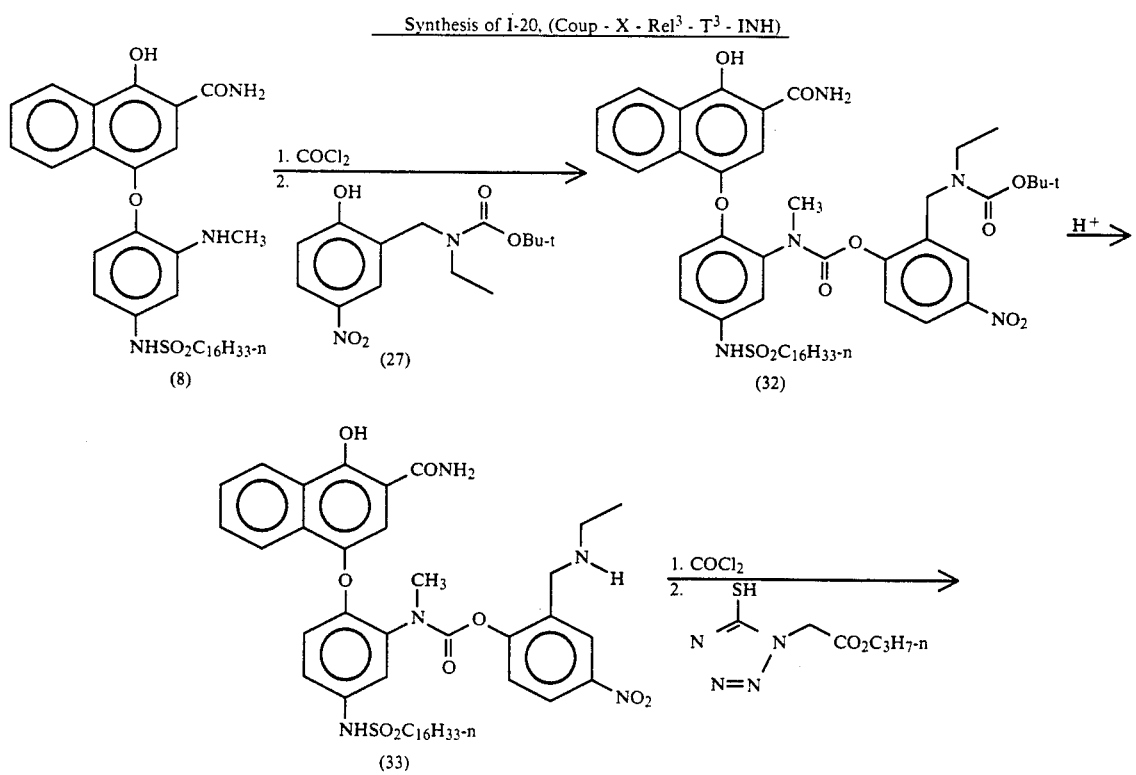

-continued
Synthesis of I-20, (Coup - X - Rel³ - T³ - INH)

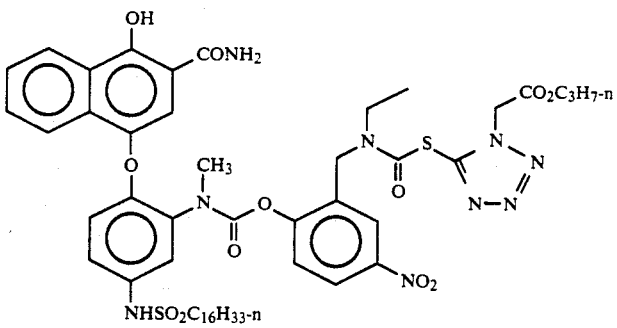

(34)-INVENTION-I-20

Compound (32)

Compound (8), (10.0 g, 16.34 mMole) was dissolved in THF (50 mL) and a 12% solution of phosgene in toluene (40 mL, 49.03 mMole) added. After stirring at room temperature for 15 minutes the solvent was removed under reduced pressure to give the crude carbamyl chloride of compound (8).

The above described carbamyl chloride (16.34 mMole), was dissolved in pyridine (100 mL) and compound (27) (5.33 g, 17.98 mMole), added. The resulting reaction solution was stirred at room temperature for 1 hour. At the end of this period the solution was concentrated under reduced pressure and the residue dissolved in ethyl acetate. The ethyl acetate solution was then washed with 2N-HCl (×1), dried (MgSO₄), filtered and concentrated to an oil. This oil was dissolved in 30% ethyl acetate in heptane and pressure chromatographed over silica gel eluting with the same solvent mixture to remove impurities and then the product compound (32), collected when the solvent was changed to 50% ethyl acetate in heptane. Yield 13.4 g, {88% from compound (8)}.

Compound (33)

Compound (32) (12.0 g, 12.85 mMole), was dissolved in dichloromethane (20 mL) and 96%-formic acid (80 mL) added. The resulting reaction solution was stirred at room temperature for 3 hours. At the end of this period the solution was poured into water and extracted with ethyl acetate. The ethyl acetate layer was collected, washed with water (×3), dried (MgSO₄), filtered and concentrated under reduced pressure to give compound (33). Yield 9.5 g, (89%).

Compound (34) - Invention I-20

Compound (33) (5.0 g, 6.00 mMole), was dissolved in THF (50 mL) and a solution of 20% phosgene in toluene (6.7 mL, 13.49 mMole) added and the resulting reaction solution stirred at room temperature for 2 hours. At the end of this period the solution was concentrated under reduced pressure to yield the carbamyl chloride of compound (33).

The above described carbamyl chloride (6.00 mMole), was dissolved in pyridine (40 mL). To this solution was added the cyclohexylamine salt of n-propyl 2,5-dihydro-5-thioxo-1H-tetrazole-1-acetic acid (2.0 g, 6.59 mMole) and the resulting solution stirred at room temperature for 2 hours. At the end of this time the reaction solution was diluted with ethyl acetate and this solution washed with 2N-HCl (×1), 2.5%-Na₂CO₃ (×3), 2N-HCl (×1), dried (MgSO₄), filtered and concentrated under reduced pressure. The residue was dissolved in 35% ethyl acetate in heptane and pressure chromatographed eluting with the same solvent mixture to remove traces of impurities. Compound (34) Invention -I-20, was collected when the solvent was changed to 50% ethyl acetate in heptane. Yield 2.5 g, {39% from compound (33)}. m/z: By FDMS molecular ion at 1061.

Synthesis of I-23, (Coup - X - Rel⁴ - T⁴ - INH)

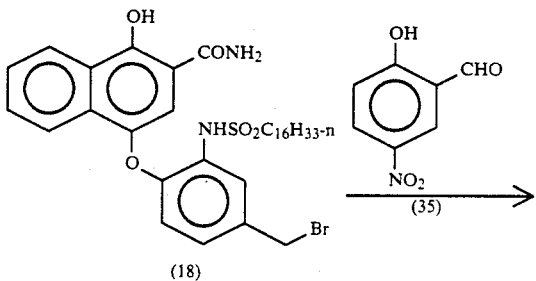

Synthesis of I-23, (Coup - X - Rel⁴ - T⁴ - INH)
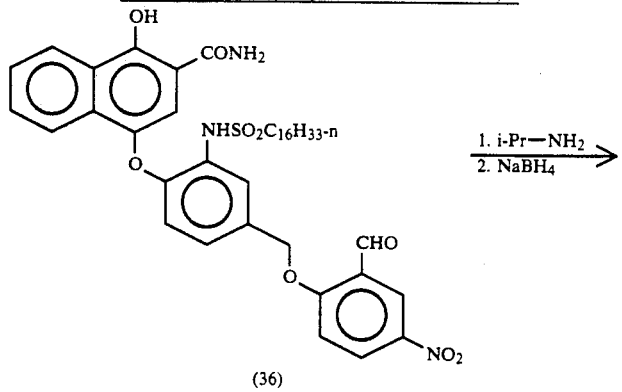
(36)
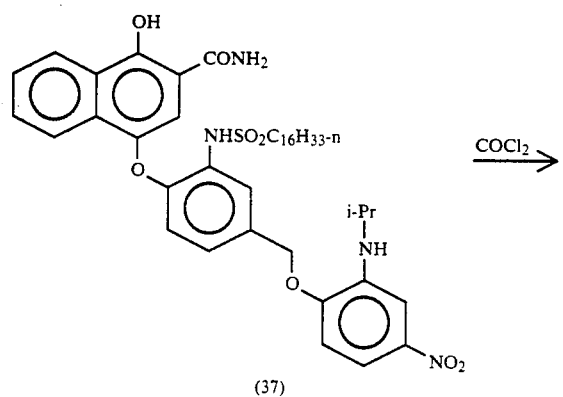
(37)
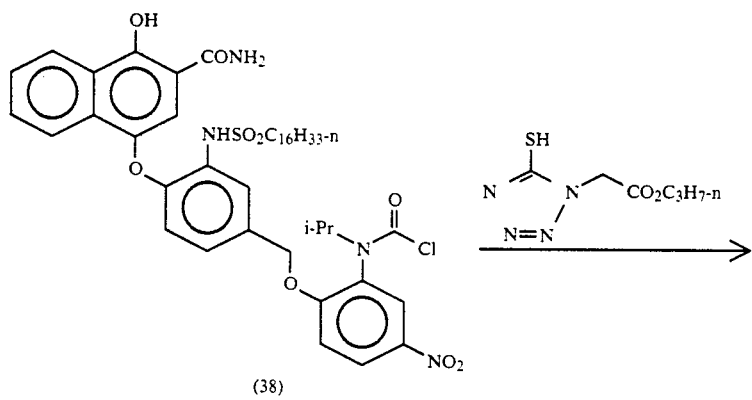
(38)
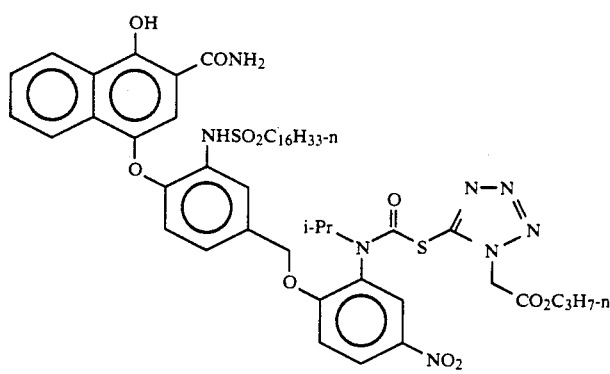
(39)-INVENTION I-23
Compound (36)
Compound (18) (14.0 g, 20.72 mMole), 2-hydroxy-5-nitrobenzaldehyde (35) (3.8 g, 22.74 mMole), potassium iodide (5,16 g, 31.08 mMole) and 2,6-lutidine (4.8 mL, 41.4 mMole) were suspended in acetonitrile (100 mL) and heated under nitrogen at 70° C. for 12 hours. At the end of this period the reaction mixture was cooled, poured into 2N-HCl and extracted with ethyl acetate (×3). The ethyl acetate layers were combined, washed with 2.5%-Na$_2$CO$_3$ (×3), 2N-HCl (×1), dried (MgSO$_4$), filtered and concentrated under reduced pressure. The residual oil was dissolved in a solvent mixture of ethyl acetate (15) heptane (35) and dichloromethane (5) and pressure chromatographed over silica gel eluting with the same solvent mixture. This removed some impurities. The product compound (36), was collected when the solvent was changed to 50% ethyl acetate in heptane. Yield 7.0 g, (44%).

Compound (37)

Compound (36) (8.0 g, 10.5 mMole), was suspended in methanol (80 mL) and just enough THF added to bring about dissolution. To this solution was added isopropylamine (4.5 mL, 52.50 mMole) and the resulting reaction mixture heated to reflux on a steam bath for 4 hours. At the end of this time the reaction was cooled to give the amine of compound (36).

Without isolation, the above described amine was cooled to 0° C. and with good stirring treated gradually with sodium borohydride (0.4 g, 50 mMole). After the sodium borohydride had been added the reaction mixture was allowed to reach room temperature over a 30 minute period. The reaction mixture was then poured into water (1L) and with 2N-HCl the pH adjusted to 1. The resulting precipitate compound (37), was filtered off, washed well with water and air-dried. Yield 8.0 g {(96%).from compound (36)}.

Compound (38)

Compound (37) (4.0 g, 4.9 mMole), was dissolved in THF (40 mL) to which was then added a 20% solution of phosgene in toluene (7.4 mL, 14.9 mMole), followed by N,N-dimethylaniline (0.63 mL, 4.9 mMole). The reaction mixture was then stirred at room temperature for 30 minutes. At the end of this period the solvent was removed under reduced pressure and the residue, containing compound (38), was taken on to the next step in the sequence. The yield was assumed to be 100%.

Compound (39) - Invention I-23

The above described carbamyl chloride compound (38) (4.9 mMole), was dissolved in dry pyridine (50 mL) and the cyclohexylamine salt of n-propyl 2,5-dihydro-5-thioxo-1H-tetrazole-1-acetic acid (1.48 g, 4.9 mMole) added. The resulting reaction solution was stirred at room temperature for 12 hours. At the end of this period the solvent was removed under reduced pressure and the residue dissolved in ethyl acetate. The ethyl acetate solution was then washed with 2N-HCl (×1), 2.5%-Na$_2$CO$_3$ (×3), 2N-HCl (×1), dried (MgSO$_4$), filtered and concentrated under reduced pressure. The resulting oil was dissolved in 30% ethyl acetate in heptane and pressure chromatographed over silica gel eluting with the same solvent mixture. The major band was collected to give compound (39) - Invention 23. Yield 0.9 g, {18%.from compound (37)}. m/z: FDMS shows molecular ion as expected at 1032.

The following examples further illustrate the invention. Photographic elements were prepared by coating the following layers on a cellulose ester film support (amounts of each component are indicated in mg/m$^2$)

| | |
|---|---|
| Emulsion layer 1: | Gelatin - 2420; red sensitized silver bromoiodide (as Ag) - 1615; yellow image coupler dispersed in dibutyl phthalate (RECEIVER LAYER) |
| Interlayer: | Gelatin - 860; didodecylhydroquinone - 113 |
| Emulsion layer 2: | Gelatin - 2690; green sensitized silver bromoiodide (as Ag) - 1615; magenta image coupler dispersed in tritolyl phosphate; DIR compound of Tables 1, 2, 3 and 4 dispersed in N,N-diethyl-dodecanamide and coated at a level sufficient to provide a contrast of 0.5 (half) of the original contrast after stepwise green light exposure and process (CAUSER LAYER) |
| Protective Overcoat | Gelatin - 5380; bisvinylsulfonylmethyl ether at 2% total gelatin. |

Structures of the image couplers are as follows:

MAGENTA IMAGE COUPLER:

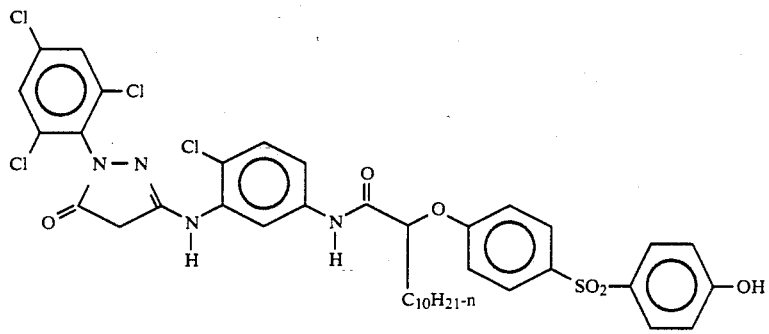

YELLOW IMAGE COUPLER:

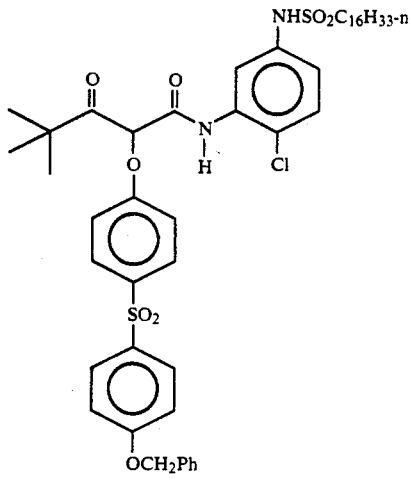

Strips of each element were exposed to green light through a graduated density step tablet, or through a 35% modulation fringe chart for sharpness measurements, and then developed 3.25 minutes at 38° C. in the following color developer, stopped, washed, bleached, fixed, washed and dried.

| Color Developer: | | |
|---|---|---|
| Distilled Water | 800 | mL |
| Sodium Metabisulfite | 2.78 | g |
| Sodium Sulfite, anhydrous | 0.38 | g |
| CD-4 (color developer)* | 4.52 | g |
| Potassium Carbonate, anhyd. | 34.3 | g |
| Potassium Bicarbonate | 2.32 | g |
| Sodium Bromide | 1.31 | g |
| Potassium Iodide | 1.20 | mg |
| Hydroxylamine Sulfate (HAS) | 2.41 | g |
| Diethylenetriaminepentacetic acid, pentasodium salt (40% Soln.) | 8.43 | g |
| Distilled Water | to 1 | L |
| Adjust pH to 10.0. | | |

*CD-4 is 4-amino-3-methyl-N-ethyl-N-beta-hydroxy-ethylaniline sulfate.

Processed images were read with green light to determine the contrast and AMT acutance. from plots of AMT acutance vs. the logarithm of the contrast for variations in the coated level of each development inhibitor releasing (DIR) compound, the acutance was determined at a contrast of 0.5 compared to its original contrast without the presence of the DIR compound. The acutance for the control DIR coupler was subtracted from each AMT value to provide the relative sharpness value reported as change in AMT in Tables 1, 2, 3, and 4. AMT calculations employed the following formula in which the cascaded area under the system modulation curve is shown in equation (21.104) on page 629 of the "Theory of the Photographic Process", 4th Edition, 1977, edited by T. H. James: AMT=100+6-6Log[cascaded area/2.6696M[ wherein the magnification factor M is 3.8 for the 35 mm system AMT. The use of CMT acutance is described by R. G. Gendron in "An Improved Objective Method of Rating Picture Sharpness: CMT acutance: in the Journal of SMPTE, Vol. 82, pages 1009-12, (1973). AMT is a further modification of CMT useful for evaluation systems which include the viewing of a positive print made from a negative.

Interimage effect (the degree of color correction) was evaluated after a daylight exposure. Interimage effect, as reported in Tables 1, 2, 3, and 4, was quantified as the ratio of the gamma ($\gamma$) of the green-sensitive layer (causer) to that of the red-sensitive layer (receiver).

TABLE 1

(Coup - X - Rel$^1$ - T$^1$ INH)

| DI(A)R Coupler | Change In Acutance ($\Delta$AMT) | Change In $\gamma$ Causer/$\gamma$ Receiver ($\Delta$IIE) |
|---|---|---|
| Control 1-A | 0 | 0 |
| Comparison 1-B* | 1.2 | 0.2 |
| Invention I-1 | 3.1 | 0.4 |
| Invention I-2 | 4.4 | 0.6 |
| Invention I-3 | 3.5 | 0.6 |
| Invention I-4 | 3.5 | 0.4 |
| Invention I-5 | 4.4 | 0.5 |
| Invention I-6 | 3.0 | 0.6 |
| Invention I-7 | 3.6 | 0.7 |
| Invention I-8 | 3.6 | 0.7 |
| Invention I-9 | 4.0 | 0.6 |
| Invention I-10 | 3.5 | 1.0 |
| Invention I-11 | 3.2 | 1.73 |
| Invention I-12 | 2.9 | 0.32 |

*Example 33, Col 45, U.S. Pat. No. 4,861,701

TABLE 2

(Coup - X - Rel$^2$ - T$^2$ INH)

| DI(A)R Coupler | Change In Acutance ($\Delta$AMT) | Change In $\gamma$ Causer/$\gamma$ Receiver ($\Delta$IIE) |
|---|---|---|
| Control 1-A | 0 | 0 |
| Comparison 1-B | 1.2 | 0.2 |
| Invention I-13 | 3.1 | 0.4 |
| Invention I-14 | 4.0 | 0.3 |
| Invention I-15 | 4.0 | 0.3 |
| Invention I-16 | 4.0 | 0.8 |

TABLE 3

(Coup - X - Rel$^3$ - T$^3$ INH)

| DI(A)R Coupler | Change In Acutance ($\Delta$AMT) | Change In $\gamma$ Causer/$\gamma$ Receiver ($\Delta$IIE) |
|---|---|---|
| Control 1-A | 0 | 0 |
| Comparison 1-B | 1.2 | 0.2 |
| Invention I-17 | 1.4 | 0.56 |
| Invention I-18 | 6.0 | 0.56 |
| Invention I-19 | 1.2 | 0.56 |
| Invention I-20 | 4.0 | 0.56 |

TABLE 3-continued

| | (Coup - X - Rel³ - T³ INH) | |
|---|---|---|
| DI(A)R Coupler | Change In Acutance (ΔAMT) | Change In γ Causer/γ Receiver (ΔIIE) |
| Invention I-21 | 0.8 | 0.27 |

TABLE 4

| | (Coup - X - Rel⁴ - T⁴ INH) | |
|---|---|---|
| DI(A)R Coupler | Change In Acutance (ΔAMT) | Change In γ Causer/γ Receiver (ΔIIE) |
| Control 1-A | 0 | 0 |
| Comparison 1-B | 1.2 | 0.2 |
| Invention I-22 | 1.4 | 0.26 |
| Invention I-23 | 6.0 | 0.26 |
| Invention I-24 | 2.1 | 0.40 |
| Invention I-25 | 7.0 | 0.19 |

TABLE 5

| | (Coupler Stability) |
|---|---|
| DI(A)R Coupler | % Loss After 2 Weeks (49° C./50% RH) |
| Control 1-A | 8.0 |
| Comparison 1-B | 20.0 |
| Invention I-1 | 3.0 |
| Invention I-2 | 11.0 |
| Invention I-3 | 0.0 |
| Invention I-4 | 0.0 |
| Invention I-6 | 0.0 |
| Invention I-7 | 0.0 |
| Invention I-8 | 3.0 |
| Invention I-9 | 1.0 |
| Invention I-10 | 0.0 |
| Invention I-11 | 2.0 |
| Invention I-12 | 0.0 |
| Invention I-13 | 0.0 |
| Invention I-14 | 0.0 |
| Invention I-15 | 5.4 |
| Invention I-16 | 1.5 |

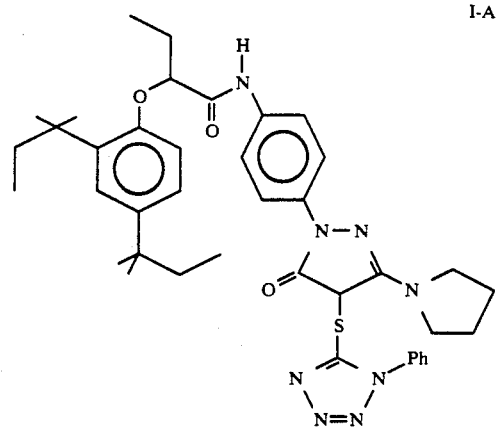

I-A (control)

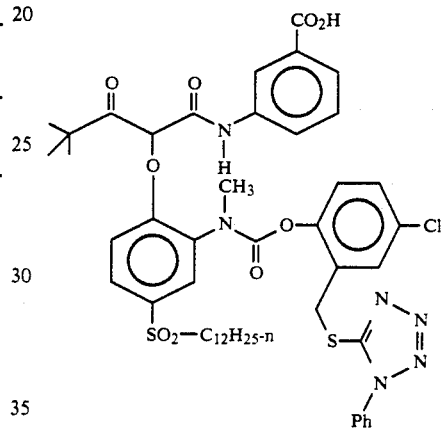

I-B (Comparison)

TABLE 1

Couplers I-1 through I-12,

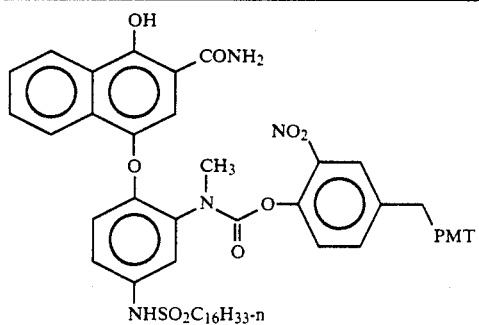

I-1 (Invention)

TABLE 1-continued
Couplers I-1 through I-12.
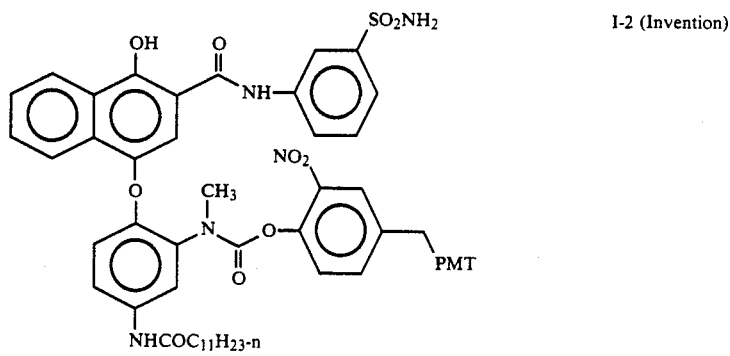
I-2 (Invention)
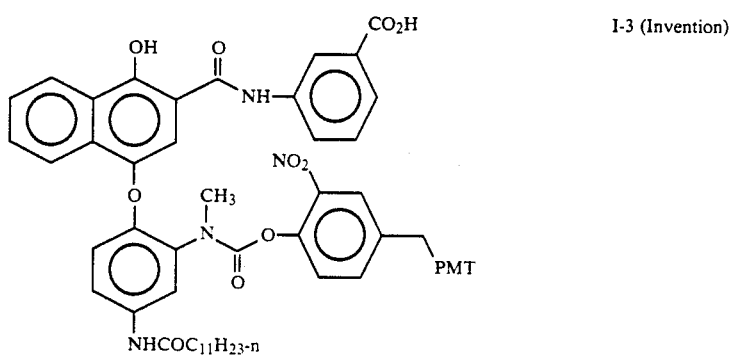
I-3 (Invention)
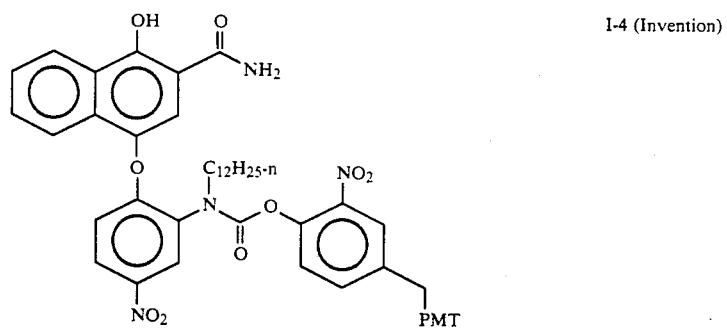
I-4 (Invention)
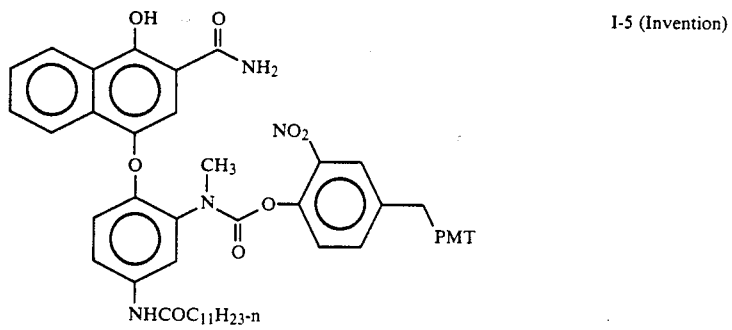
I-5 (Invention)

TABLE 1-continued
Couplers I-1 through I-12.
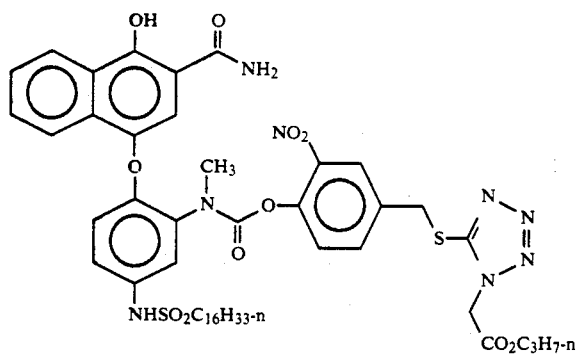
I-6 (Invention)
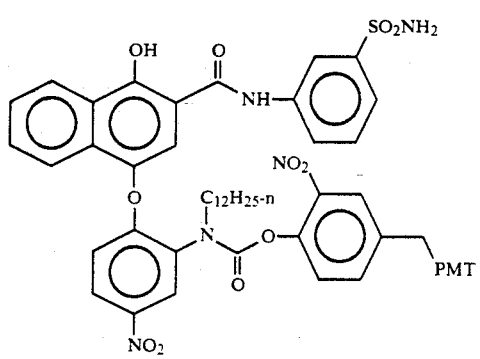
I-7 (Invention)
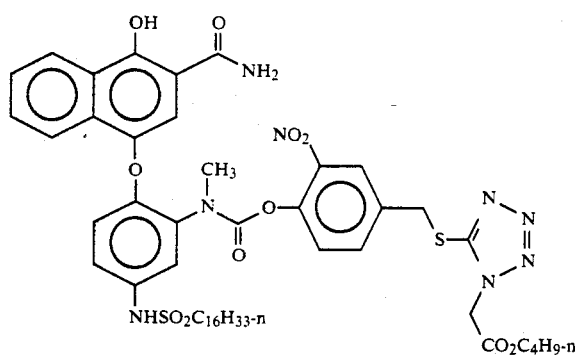
I-8 (Invention)
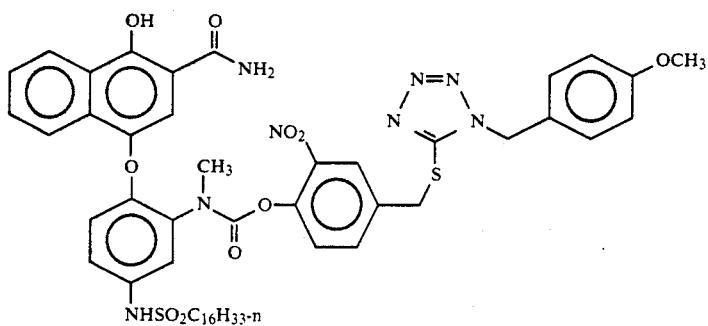
I-9 (Invention)

TABLE 1-continued
Couplers I-1 through I-12,
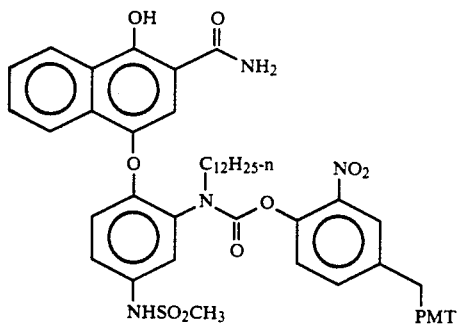
I-10 (Invention)
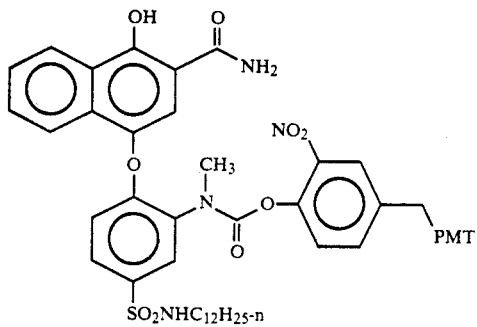
I-11 (Invention)
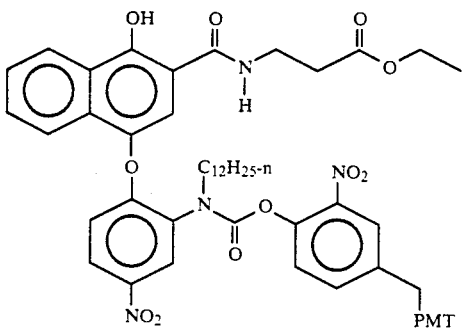
I-12 (Invention)
TABLE 2
Couplers I-13 through I-16,
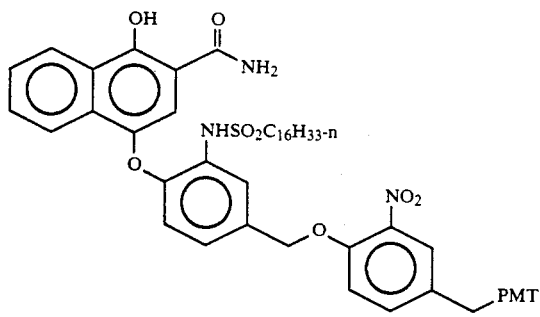
I-13 (Invention)

TABLE 2-continued
Couplers I-13 through I-16.
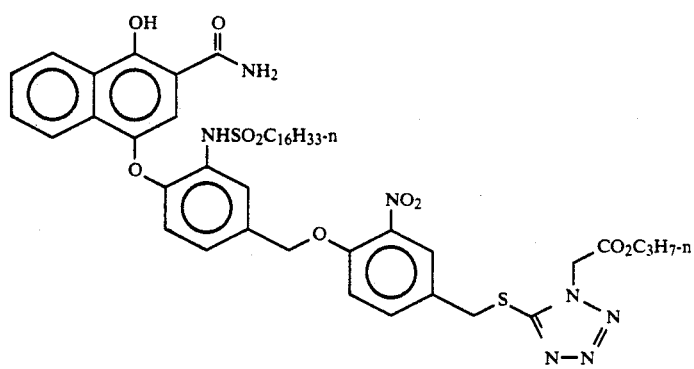
I-14 (Invention)
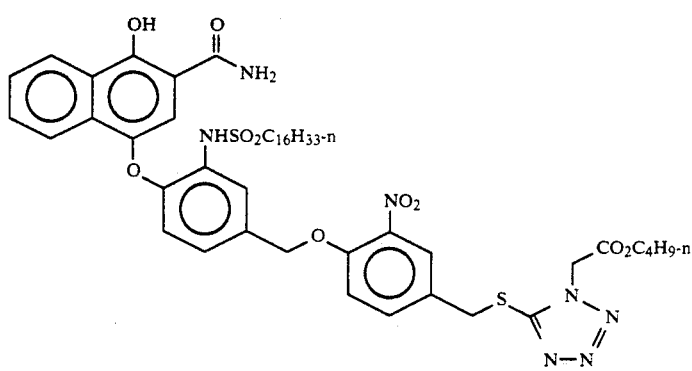
I-15 (Invention)
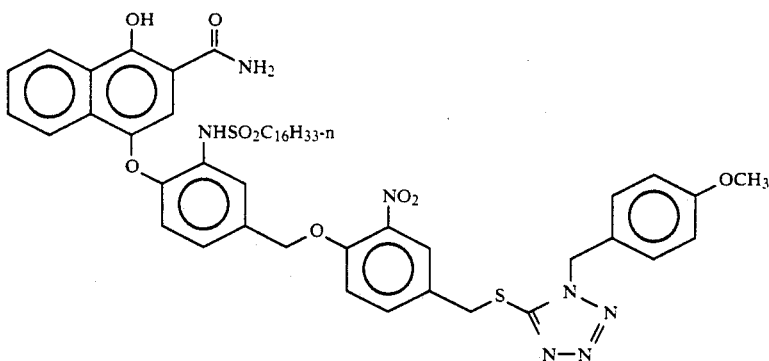
I-16 (Invention)
TABLE 3
Couplers I-17 through I-21.
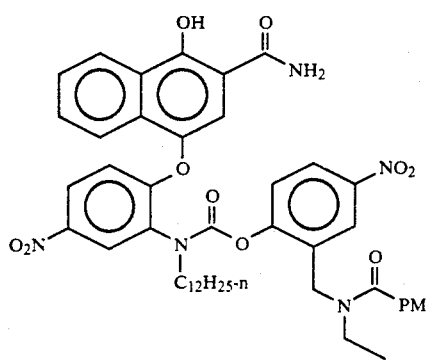
I-17 (Invention)

TABLE 3-continued
Couplers I-17 through I-21.
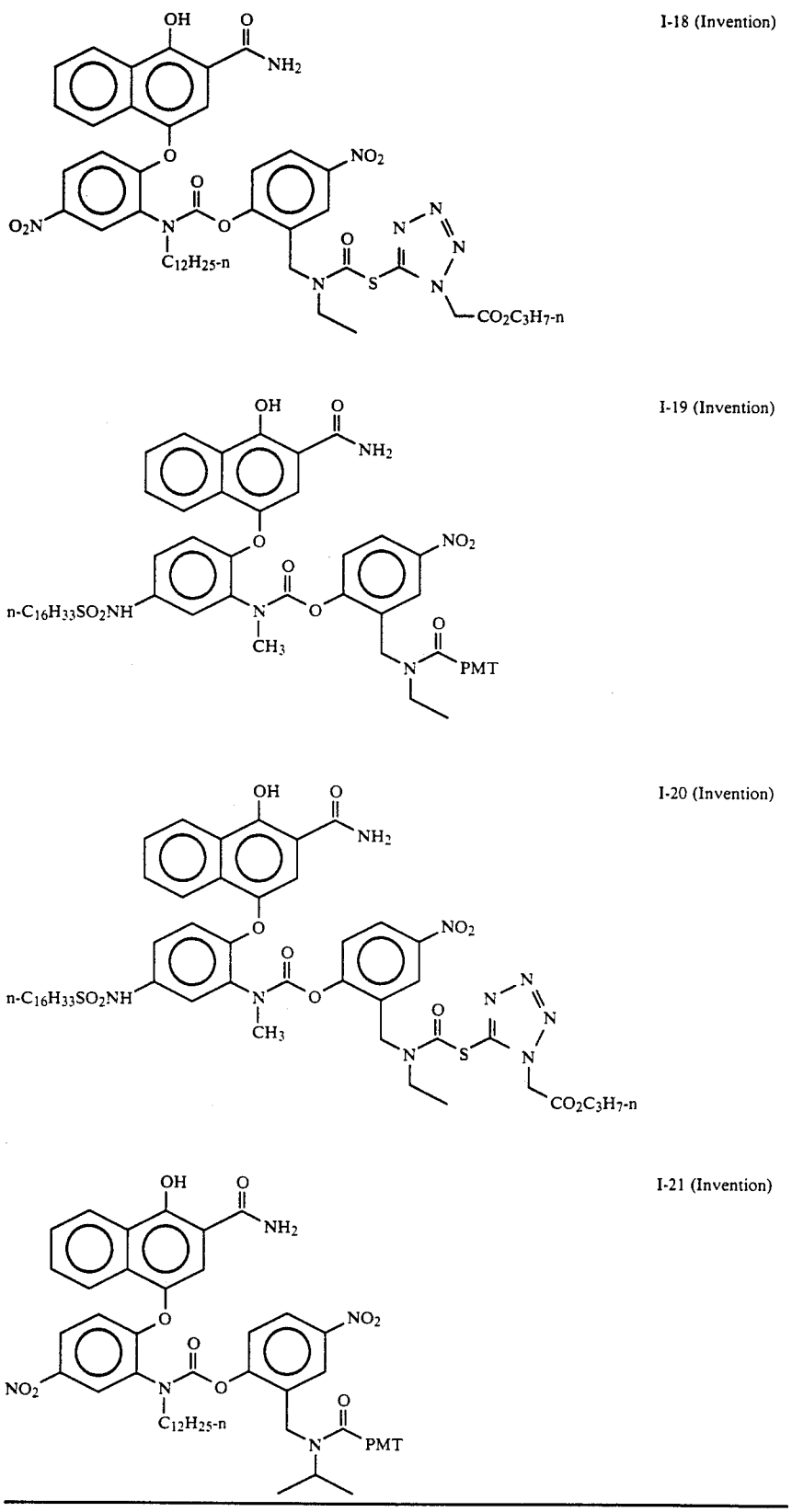
I-18 (Invention)
I-19 (Invention)
I-20 (Invention)
I-21 (Invention)

TABLE 4
Couplers I-22 through I-25.
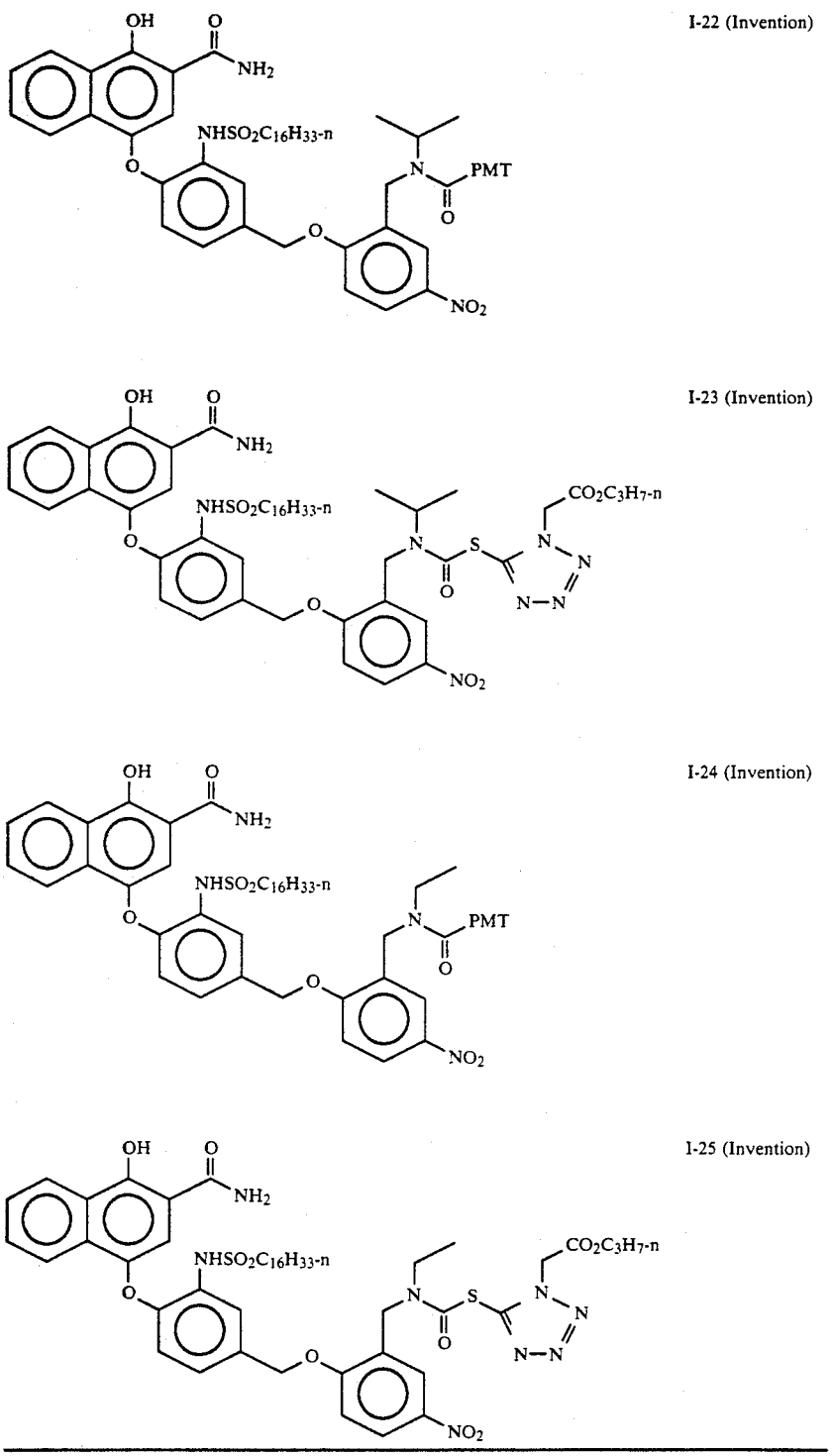
I-22 (Invention)
I-23 (Invention)
I-24 (Invention)
I-25 (Invention)
Further examples of couplers of the invention are as follows:

-continued
Further examples of couplers of the invention are as follows:
I-26 (Invention)
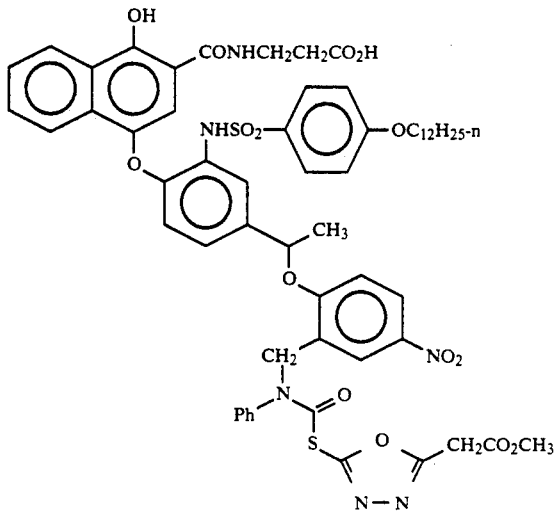
I-27 (Invention)
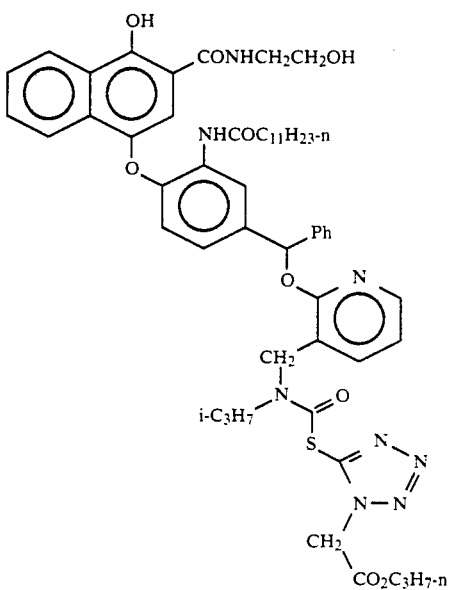
I-28 (Invention)
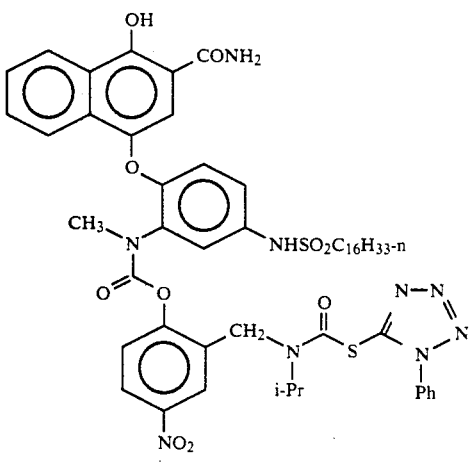

-continued
Further examples of couplers of the invention are as follows:
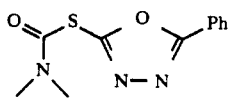
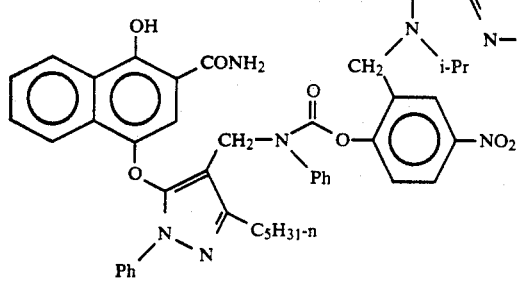
I-29 (Invention)
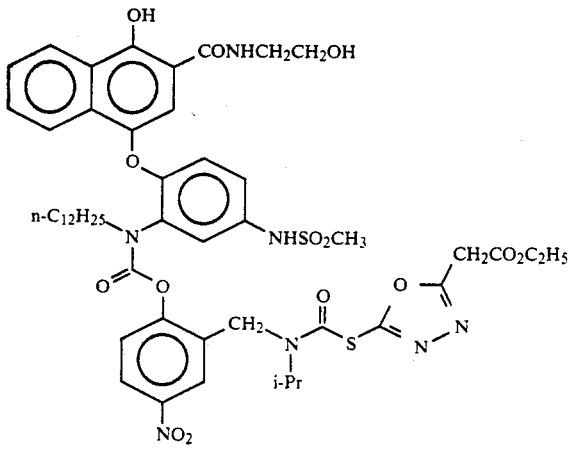
I-30 (Invention)
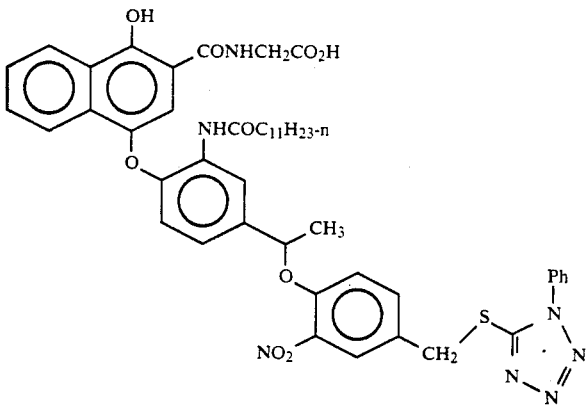
I-31 (Invention)
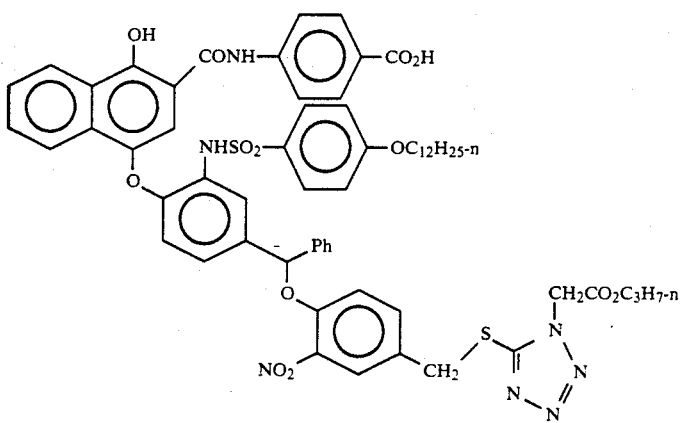
I-32 (Invention)

-continued
Further examples of couplers of the invention are as follows:
I-33 (Invention)
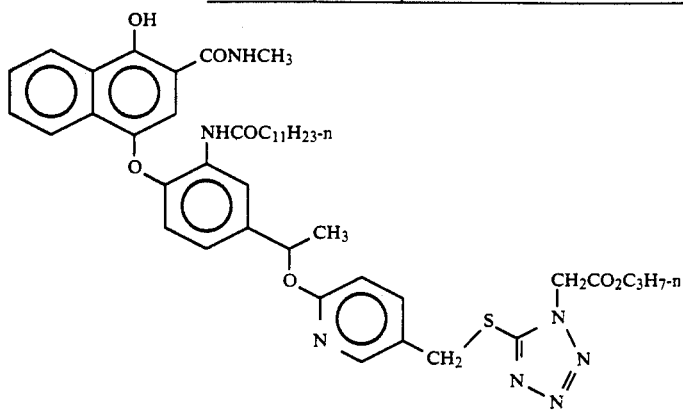
I-34 (Invention)
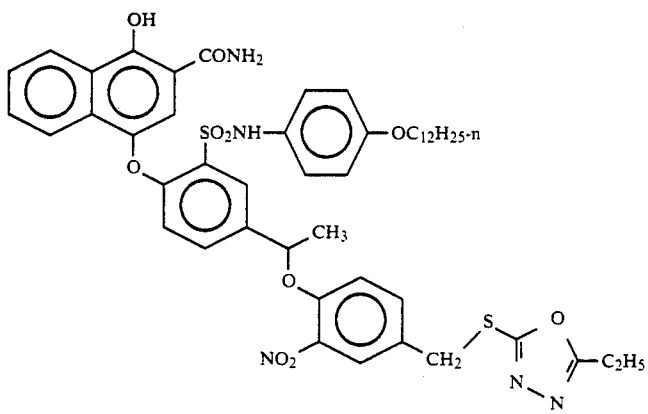
I-35 (Invention)
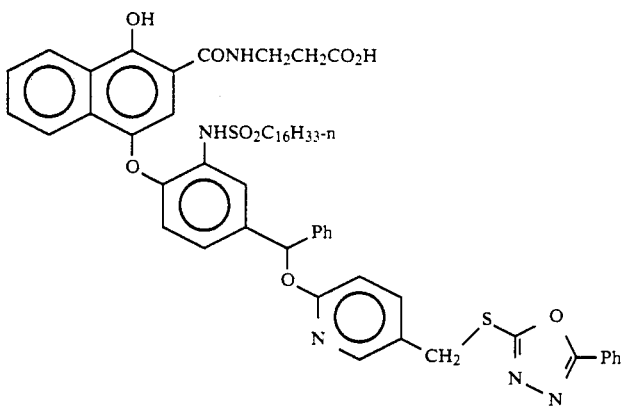
I-36 (Invention)
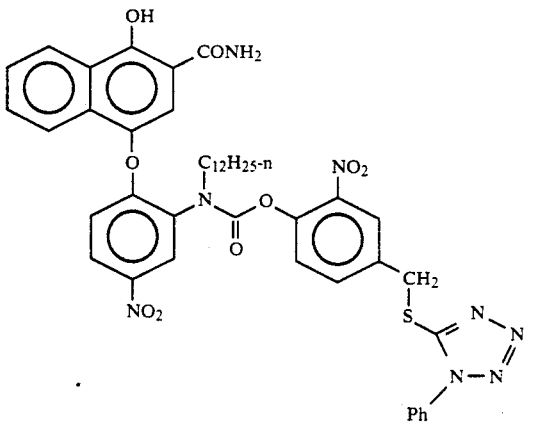

-continued
Further examples of couplers of the invention are as follows:

I-37 (Invention)
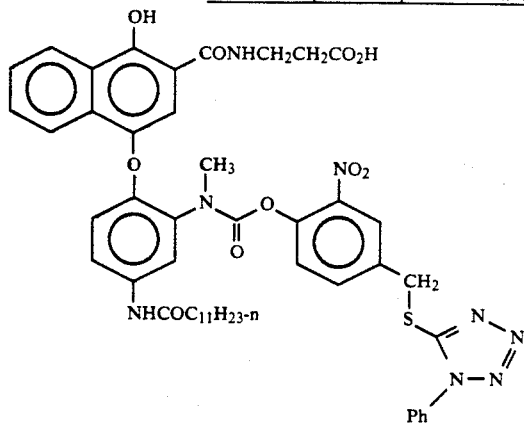

I-38 (Invention)
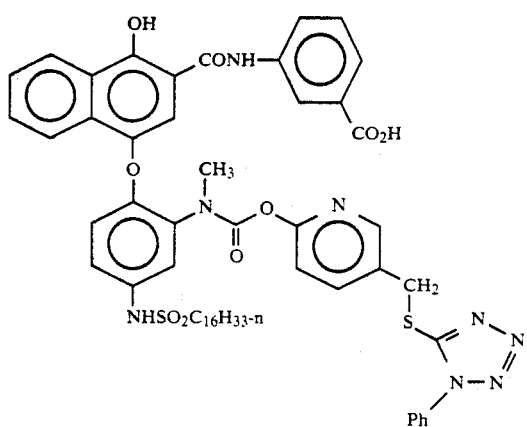

I-39 (Invention)
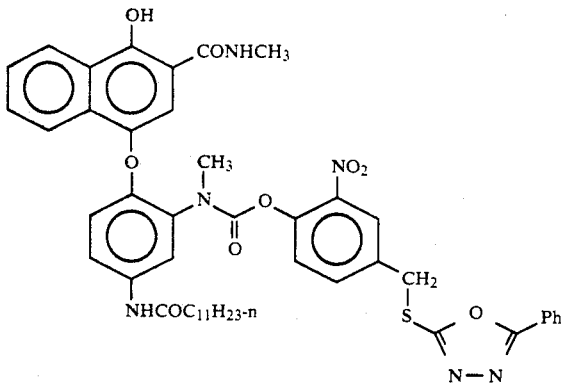

I-40 (Invention)
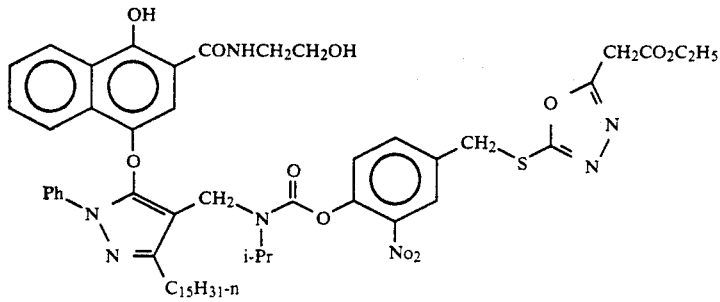

PMT herein means a phenylmercaptotetrazole group.
Ph herein means a phenyl group.

From Tables 1, 2, 3, 4 and 5 it can be seen that the compounds of the invention give improved acutance, interlayer interimage and stability over the Control 1-A and the Comparison 1-B. That is for example, in Table 5 Couplers I-1 and I-3 showed no loss in stability.

The invention has been described in detail with particular reference to preferred embodiments thereof, but it will be understood that variations and modifications can be effected within the spirit and scope of the invention.

What is claimed is:

1. In a method of preparing a washout photographic coupler comprising a coupler moiety (COUP) containing a substituted or unsubstituted ballasted releasing group (A) selected from aryloxy, thioaryloxy, heterocyclicoxy, and thioheterocyclicoxy releasing groups having attached thereto a phenoxy timing group containing a photographically useful group (PUG), the releasing group capable of elimination electron transfer to release said timing group, the method comprising: (a) providing a coupler moiety (COUP) having said releasing group (A) in a coupling off position, said releasing group (A) having on at least one of the 2- or 4-position a substituted or unsubstituted halomethyl; (b) reacting a substituted or unsubstituted hydroxyaryl aldehyde or hydroxyaryl ketone with said halomethyl group of step (a) in the presence of an organic base and a solvent to form a first product; and thereafter (c) reducing said first product and halogenating said reduced first product before reacting with a photographically useful group to form said washout photographic coupler; wherein the improvement comprises using in step (b) an alkylpyridine for said organic base, and a dipolar aprotic solvent for said solvent.

2. The method in accordance with claim 1 wherein the halomethyl is substituted with at least one of hydrogen, substituted or unsubstituted alkyl and substituted or unsubstituted aryl.

3. The method in accordance with claim 1 wherein the alkypyridine is selected from mono-, di-, and trialkylpyridine.

4. The method in accordance with claim 1 wherein the aprotic solvent is selected from dimethylformamide, dimethylacetamide, and acetonitrile.

5. The method in accordance with claim 3 wherein the alkylpyridine is a dialkylpyridine.

6. The method in accordance with claim 5 wherein dialkylpyridine is 2,6-lutidine.

7. The method in accordance with claim 1 wherein potassium iodide is added to the reaction in step (b) to increase the rate of reaction.

8. The method in accordance with claim 1 wherein hydroxyaryl aldehyde or hydroxyaryl ketone has the hydroxy group in the 2- or 4-position to the aldehyde or ketone groups.

9. The method in accordance with claim 1 wherein the halomethyl is selected from bromomethyl and chloromethyl.

10. A process of forming a compound of the formula:

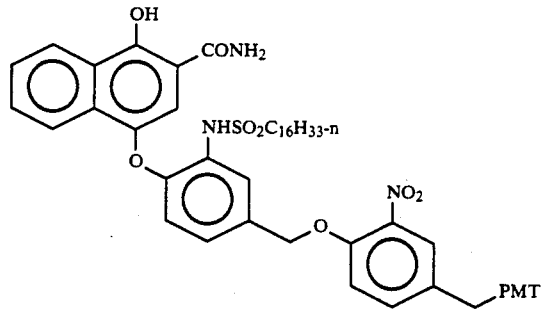

wherein PMT is phenylmercaptotetrazole; comprising reacting a compound of formula:

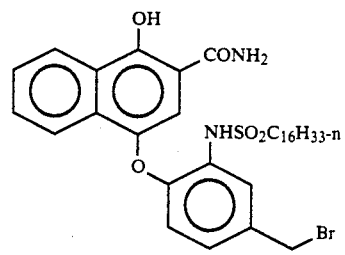

with:

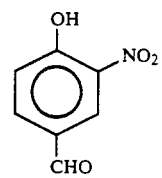

in the presence of 2,6-lutidine in dimethylacetamide; then reacting aldehyde product with sodium borohydride to form the corresponding —$CH_2OH$ compound; then reacting the resulting —$CH_2OH$ compound with $PBr_3$ in ether to form the resulting —$CH_2Br$ compound; and then reacting the resulting —$CH_2Br$ compound with sodium phenylmercaptotetrazole.

* * * * *